US005654174A

United States Patent [19]
Cohen et al.

[11] Patent Number: 5,654,174
[45] Date of Patent: Aug. 5, 1997

[54] HERPES SIMPLEX VIRUS GLYCOPROTEIN D VARIANTS

[75] Inventors: Gary H. Cohen, Havertown, Pa.; Roselyn J. Eisenberg, Haddonfield, N.J.; Anthony Nicola, Philadelphia, Pa.

[73] Assignee: Competitive Technologies, Inc., Westport, Conn.

[21] Appl. No.: 499,568

[22] Filed: Jul. 7, 1995

[51] Int. Cl.$^6$ .......................... C12P 21/02; C07K 14/035; C12N 15/38; C12N 5/10

[52] U.S. Cl. ................... 435/69.3; 435/348; 435/252.3; 435/320.1; 435/235.1; 435/365; 530/350; 536/23.72; 930/224; 424/186.1

[58] Field of Search ..................... 435/69.3, 235.1, 435/252.3, 240.2, 320.1; 530/350, 395; 424/130.1, 131.1, 141.1, 186.1, 199.1, 204.1; 536/23.1, 23.72; 930/224

[56] References Cited

U.S. PATENT DOCUMENTS

| | | | |
|---|---|---|---|
| 4,709,011 | 11/1987 | Cohen et al. | 530/324 |
| 4,762,708 | 8/1988 | Cohen et al. | 424/186.1 |
| 5,149,660 | 9/1992 | Cohen et al. | 436/87 |

OTHER PUBLICATIONS

Johnson, et al. J. Virol. 62:4506–4612 1988.
Cai et al., "Herpes Simplex Virus Type 1 ICP0 Plays a Critical Role in the De Novo Synthesis of Infectious Virus following Transfection of Viral DNA," *J. Virol.*, 63(11):4579–4589 (1989).
Chiang et al. "Identification of Functional Regions of Herpes Simplex Virus Glycoprotein gD by Using Linker-Insertion Mutagenesis," *J. Virol.*, 68(4):2529–2543 (1994).
Cohen et al. "Expression of Herpes Simplex Virus Type 1 Glycoprotein D Deletion Mutants in Mammalian Cells," *J. Virol.*, 62(8):1932–1940 (1988).
Fields and Knipe, Eds., *Fundamental Virology*, Chapter 16, Raven Press, New York (1986).
Hill et al., "Trauma to the Skin Causes Recurrence of Herpes Simplex in the Mouse," *J. gen. Virol.*, 39: 21–28 (1978).
Hill et al., "Adrenergically induced recurrent HSV–1 corneal epithelial lesions," *Curr. Eye Res.*, 6(8): 1065–1071 (1987).
Johnson et al., "Soluble Forms of Herpes Simplex Virus Glyoprotein D Bind to a Limited Number of Cell Surgace Receptors and Inhibit Virus Entry into Cells," *J. Virol.*, 64(6): 2569–2576 (Jun. 1990).
Kunkel et al., "Rapid and Efficient Site–Specific Mutagenesis without Phenotypic Selection," *Methods Enzymol.*, 154: 367–382 (1987).
Landolfi et al., "Baculovirus–expressed herpes simplex virus type 2 glycoprotein D is immunogenic and protective against lethal HSV challenge," *Vaccine*, 11: 407–414 (1993).
Ligas and Johnson, "A Herpes Simplex Virus Mutant in Which Glycoprotein D Sequences Are Replaced by β–Galactosidase Sequences Binds to but Is Unable To Penetrate into Cells," *J. Virol.*, 62(5): 1486–1494 (1988).

Long et al., "Glycoprotein D Protects Mice Against Lethal Challenge with Herpes Simplex Virus Types 1 and 2," *Infect. Immun.* 37(2): 761–764 (1984).
Martin et al.; "Soluble Glycoprotein D Blocks Herpes Simplex Virus Type 1 Infection of Rat Eyes," *J. Virol.*, 66(9): 5183–5189 (Sep. 1992).
Metcalf et al., "Herpetic Keratitis in Athymic (Nude) Mice," *Infect, Immun.*, 26(3): 1164–1171 (1979).
Muggeridge et al., "Identification of a Site on Herpes Simplex Virus Type 1 Glycoprotein D That Is Essential for Infectivity," *J. Virol.*, 64(8): 3617–3626 (1990).
Rock and Fraser, "Detection of HSV–1 genome in central nervous system of latently infected mice," *Nature*, 302(7): 523–525 (1983).
Sisk et al., "High–Level Expression and Purification of Secreted Forms of Herpes Simplex Virus Type 1 Glycoprotein gD Synthesized by Baculovirus–Infected Insect Cells," *J. Virol.*, 68(2): 766–775 (1994).
Stanberry et al., "Genital Herpes in Guinea Pigs: Pathogenesis of the Primary Infection and Description of Recurrent Disease," *J. Infect. Dis.*, 146(3): 397–404 (Sep. 1982).
Stanberry, L.R., "Pathogenesis of Herpes Simplex Virus Infection and Animal Models for its Study," *Current Topics in Microbiol. and Immuno.*, 179: 15–30 (1992).
Stevens, "Humans Herpesviruses: a Consideration of the Latent State," *Microbiol. Rev.*, 53(3): 318–332 (1989).
Stevens and Cook, "Latent Herpes Simplex Virus in Spinal Ganglia of Mice," *Science*, 173: 843–845 (1971).

(List continued on next page.)

*Primary Examiner*—Mary E. Mosher
*Assistant Examiner*—Michael Chen
*Attorney, Agent, or Firm*—Marshall, O'Toole, Gerstein, Murray & Borun

[57] ABSTRACT

The present invention provides variant HSV-1 glycoprotein D and HSV-2 glycoprotein D molecules capable of preventing infection of cells by herpes simplex virus types 1 and/or 2. Also provided are novel purified and isolated polynucleotides encoding the variant gD molecules. HSV gD-1 and gD-2 region IV variants or fragments thereof are specifically contemplated by the invention. The presently preferred variant molecule gD-1(Δ290–299t) is the product of recombinant expression in Sf9 cells of a fusion protein including the signal peptide of honeybee melittin and Patton strain HSV-1 gD wherein (1) the Patton strain amino acid residues 290 through 299 of the mature gD-1 protein have been replaced with the amino acid residues arginine, lysine, isoleucine and phenylalanine, and (2) Patton strain amino acid residues 308 through 369 have been replaced with five histidine residues. When expressed in Sf9 cells, cleavage of the melittin signal peptide results in the presence of aspartate and proline residues at the amino terminus of the variant molecule. The amino acid sequence of gD-1(Δ290–299t) is set out in SEQ ID NO: 2 and the preferred DNA sequence encoding gD-1(Δ290–299t) is set out in SEQ ID NO: 1. Administration of gD variant molecules of the invention to mammalian subjects, especially humans, for the purpose of preventing HSV infection and/or ameliorating pathological sequelae of HSV infection is specifically contemplated.

11 Claims, 8 Drawing Sheets

OTHER PUBLICATIONS

Straus et al., "Suppression of Frequently Recurring Genital Herpes, A Placebo–Controlled Double–Blind Trial of Oral Acyclovir," *N. Eng. J. Med.*, 310(24): 1545–1550 (1984).

Tal–Singer et al., "Interaction of Herpes Simplex Virus Glycoprotein gC with Mammalian Cell Surface Molecules" *J. Virol.*, 69(7): 4471–4483 (1995).

Tenser, R.B., "Intracerebral Inoculation of Newborn and Adult Mice with Thymidine Kinase–Deficient Mutants of Herpes Simplex Virus Type 1," *J. Infect. Dis.*, 147: 956 (May 1983).

Tessier et al., "Enhanced secretion from insect cells of a foreign protein fused to the honeybee melittin signal peptide," *Gene*, 98: 177–183 (1991).

van Regenmortel and Neurath Eds., *Chapter 20 in Immunochemistry of Viruses, II. The Basis for Serodiagnosis and Vaccines*, Elsevier Science Publishers B.V. (1990).

Watson et al., "Herpes Simplex Virus Type–1 Glycoprotein D Gene: Nucleotide Sequence and Expression in *Escherichia coli*," *Science*, 218(22): 381–384 (Oct. 1982).

Full length gD gD-1(306t)

gD-1(Δ290-299t)

```
gD-1  KYALADASLKMADPNRFRGKDLPVLDQLTDPPGVRRVYHI          40
gD-2       P         N           K gD-1  QAGLPDPFQPPSLPITVYYAVLERACRSVLLNAPSEAPQI          80
gD-2  -PS E      I            H gD-1  VRGASEDVRKQPYNLTIAWFRMGGNCAIPITVMEYTECSY          120
gD-2      DEA HT    Y  D           P gD-1  NKSLGACPIRTQPRWNYYDSFSAVSEDNLGFLMHAPAFET          160
gD-2        V       S gD-1  AGTYLRLVKINDWTEITQFILEHRAKGSCKYALPLRIPPS          200
gD-2                  RA       A gD-1  ACLSPQYQQGVTVDSIGMLPRFIPENQRTVAVYSLKIAG           240
gD-2      TSK            L gD-1  WHGPKAPYTSTLLPPELSETPNATQPELAPEDPEDSALLE          280
gD-2       P      D T   V gD-1  DPVGTVAPQIPPNWHIPSIQDAATPYHPPATPNNMGLIAG          320
gD-2   A  SS       V  HA ASP I                        319 gD-1  AVGGSLLAALVICGIVYWMHRRTRKAPKRIRLPHIREDDQ          360
gD-2   LA T    G    AF VR AQM    L    D A              359 gD-1  PSSHQPLFY                                        369
gD-2  P                                                368
```

FIGURE 2

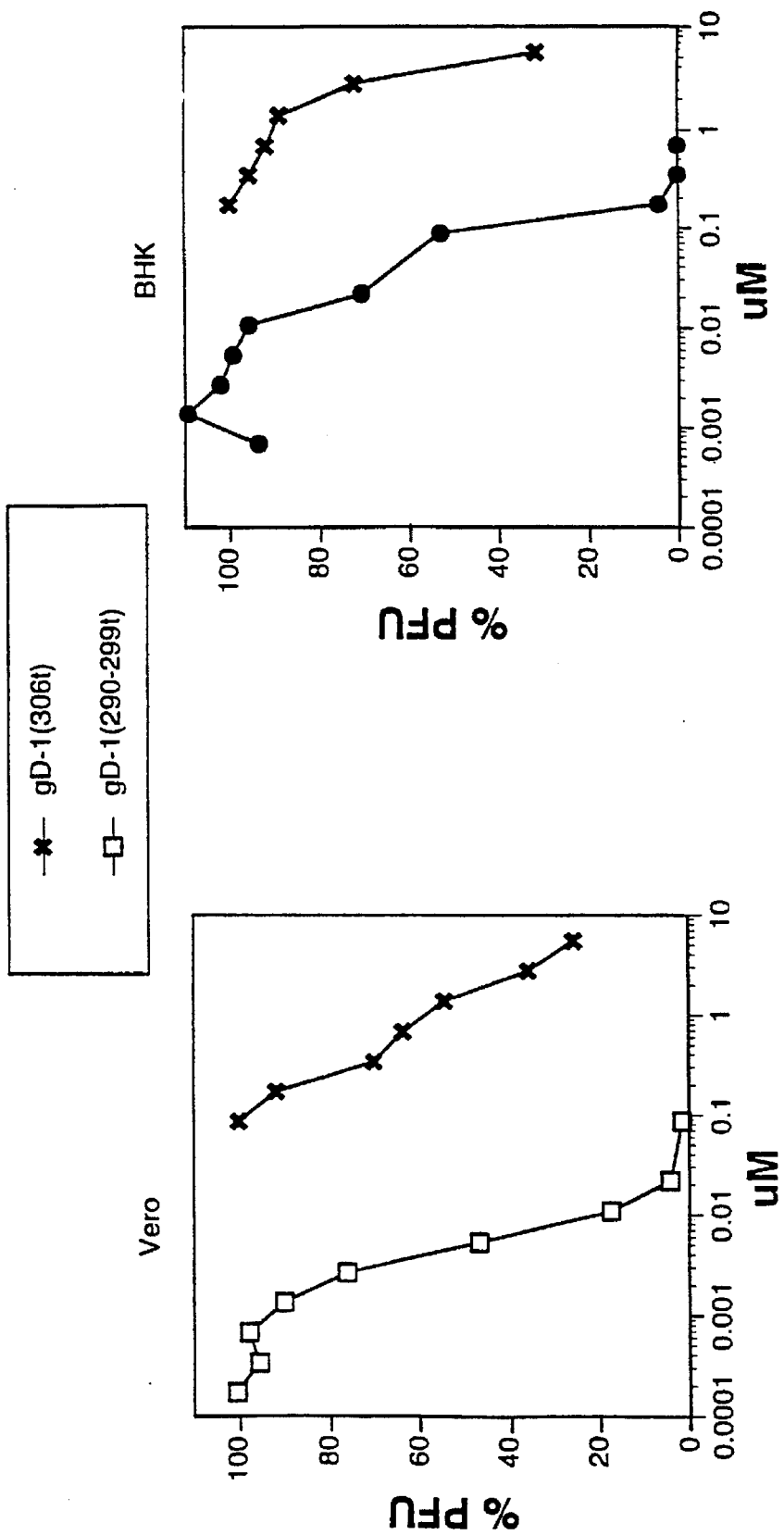

| ASSAY | WHEN ADDED | PROTEIN | | | | | | |
|---|---|---|---|---|---|---|---|---|
| | | gD-1(306t) | ∇34t | ∇126t | ∇243t | Δ290-299t | gD-2(306t) | Heat denatured gD-1(306t) | BSA |
| Plaque formation | Pre-adsorption (4°C) | 1.6 | NE | 2.4 | 4.2 | 0.004 | 0.41 | NE | NE |
| Plaque formation | Post-adsorption (4°C) | 0.45 | NE | 3.8 | 2.1 | 0.04 | | | |
| Cell to cell spread | 3 hr post infection (37°C) | 3.6 | NE | >5.6 | >5.6 | 0.19 | >5.6 | NE | NE |
| Entry* | Pre-adsorption (4°C) | 3.7 | NE | | 9.0 | 0.19 | >11.2 | NE | NE |

FIGURE 8

Shown are the uM amounts necessary for 50% inhibition of 50 PFU HSV as measured by plaque formation on Vero cells (or 50% inhibition of 1.5 x 10⁴ PFU as measured by Beta-galactosidase production*).

NE = no effect

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 927 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: CDS
        ( B ) LOCATION: 1..924

( i x ) FEATURE:
        ( A ) NAME/KEY: mat_peptide
        ( B ) LOCATION: 7..924

( x i ) SEQUENCE DESCRIPTION: SEQ ID NO:1:

```
GAT  CCC  AAA  TAT  GCC  TTG  GCG  GAT  GCC  TCT  CTC  AAG  ATG  GCC  GAC  CCC        4 8
Asp  Pro  Lys  Tyr  Ala  Leu  Ala  Asp  Ala  Ser  Leu  Lys  Met  Ala  Asp  Pro
 -2        1              5                        10

AAT  CGC  TTT  CGC  GGC  AAA  GAC  CTT  CCG  GTC  CTG  GAC  CAG  CTG  ACC  GAC        9 6
Asn  Arg  Phe  Arg  Gly  Lys  Asp  Leu  Pro  Val  Leu  Asp  Gln  Leu  Thr  Asp
```

| | | | | | | | | | | | | | | | | |
|---|---|---|---|---|---|---|---|---|---|---|---|---|---|---|---|---|
| | | 15 | | | | 20 | | | | | 25 | | | | 30 | |
| CCT | CCG | GGG | GTC | CGG | CGC | GTG | TAC | CAC | ATC | CAG | GCG | GGC | CTA | CCG | GAC | 144 |
| Pro | Pro | Gly | Val | Arg | Arg | Val | Tyr | His | Ile | Gln | Ala | Gly | Leu | Pro | Asp | |
| | | | | 35 | | | | | 40 | | | | | 45 | | |
| CCG | TTC | CAG | CCC | CCC | AGC | CTC | CCG | ATC | ACG | GTT | TAC | TAC | GCC | GTG | TTG | 192 |
| Pro | Phe | Gln | Pro | Pro | Ser | Leu | Pro | Ile | Thr | Val | Tyr | Tyr | Ala | Val | Leu | |
| | | | 50 | | | | | 55 | | | | | 60 | | | |
| GAG | CGC | GCC | TGC | CGC | AGC | GTG | CTC | CTA | AAC | GCA | CCG | TCG | GAG | GCC | CCC | 240 |
| Glu | Arg | Ala | Cys | Arg | Ser | Val | Leu | Leu | Asn | Ala | Pro | Ser | Glu | Ala | Pro | |
| | | 65 | | | | 70 | | | | | 75 | | | | | |
| CAG | ATT | GTC | CGC | GGG | GCC | TCC | GAA | GAC | GTC | CGG | AAA | CAA | CCC | TAC | AAC | 288 |
| Gln | Ile | Val | Arg | Gly | Ala | Ser | Glu | Asp | Val | Arg | Lys | Gln | Pro | Tyr | Asn | |
| | 80 | | | | | 85 | | | | | 90 | | | | | |
| CTG | ACC | ATC | GCT | TGG | TTT | CGG | ATG | GGA | GGC | AAC | TGT | GCT | ATC | CCC | ATC | 336 |
| Leu | Thr | Ile | Ala | Trp | Phe | Arg | Met | Gly | Gly | Asn | Cys | Ala | Ile | Pro | Ile | |
| 95 | | | | | 100 | | | | | 105 | | | | | 110 | |
| ACG | GTC | ATG | GAG | TAC | ACC | GAA | TGC | TCC | TAC | AAC | AAG | TCT | CTG | GGG | GCC | 384 |
| Thr | Val | Met | Glu | Tyr | Thr | Glu | Cys | Ser | Tyr | Asn | Lys | Ser | Leu | Gly | Ala | |
| | | | | 115 | | | | | 120 | | | | | 125 | | |
| TGT | CCC | ATC | CGA | ACG | CAG | CCC | CGC | TGG | AAC | TAC | TAT | GAC | AGC | TTC | AGC | 432 |
| Cys | Pro | Ile | Arg | Thr | Gln | Pro | Arg | Trp | Asn | Tyr | Tyr | Asp | Ser | Phe | Ser | |
| | | | 130 | | | | | 135 | | | | | 140 | | | |
| GCC | GTC | AGC | GAG | GAT | AAC | CTG | GGG | TTC | CTG | ATG | CAC | GCC | CCC | GCG | TTT | 480 |
| Ala | Val | Ser | Glu | Asp | Asn | Leu | Gly | Phe | Leu | Met | His | Ala | Pro | Ala | Phe | |
| | | 145 | | | | | 150 | | | | | 155 | | | | |
| GAG | ACC | GCC | GGC | ACG | TAC | CTG | CGG | CTC | GTG | AAG | ATA | AAC | GAC | TGG | ACG | 528 |
| Glu | Thr | Ala | Gly | Thr | Tyr | Leu | Arg | Leu | Val | Lys | Ile | Asn | Asp | Trp | Thr | |
| | 160 | | | | | 165 | | | | | 170 | | | | | |
| GAG | ATT | ACA | CAG | TTT | ATC | CTG | GAG | CAC | CGA | GCC | AAG | GGC | TCC | TGT | AAG | 576 |
| Glu | Ile | Thr | Gln | Phe | Ile | Leu | Glu | His | Arg | Ala | Lys | Gly | Ser | Cys | Lys | |
| 175 | | | | | 180 | | | | | 185 | | | | | 190 | |
| TAC | GCC | CTC | CCG | CTG | CGC | ATC | CCC | CCG | TCA | GCC | TGC | CTC | TCC | CCC | CAG | 624 |
| Tyr | Ala | Leu | Pro | Leu | Arg | Ile | Pro | Pro | Ser | Ala | Cys | Leu | Ser | Pro | Gln | |
| | | | | 195 | | | | | 200 | | | | | 205 | | |
| GCC | TAC | CAG | CAG | GGG | GTG | ACG | GTG | GAC | AGC | ATC | GGG | ATG | CTG | CCC | CGC | 672 |
| Ala | Tyr | Gln | Gln | Gly | Val | Thr | Val | Asp | Ser | Ile | Gly | Met | Leu | Pro | Arg | |
| | | | 210 | | | | | 215 | | | | | 220 | | | |
| TTC | ATC | CCC | GAG | AAC | CAG | CGC | ACC | GTC | GCC | GTA | TAC | AGC | TTG | AAG | ATC | 720 |
| Phe | Ile | Pro | Glu | Asn | Gln | Arg | Thr | Val | Ala | Val | Tyr | Ser | Leu | Lys | Ile | |
| | | 225 | | | | | 230 | | | | | 235 | | | | |
| GCC | GGG | TGG | CAC | GGG | CCC | AAG | GCC | CCA | TAC | ACG | AGC | ACC | CTG | CTG | CCC | 768 |
| Ala | Gly | Trp | His | Gly | Pro | Lys | Ala | Pro | Tyr | Thr | Ser | Thr | Leu | Leu | Pro | |
| | 240 | | | | | 245 | | | | | 250 | | | | | |
| CCG | GAG | CTG | TCC | GAG | ACC | CCC | AAC | GCC | ACG | CAG | CCA | GAA | CTC | GCC | CCG | 816 |
| Pro | Glu | Leu | Ser | Glu | Thr | Pro | Asn | Ala | Thr | Gln | Pro | Glu | Leu | Ala | Pro | |
| 255 | | | | | 260 | | | | | 265 | | | | | 270 | |
| GAA | GAC | CCC | GAG | GAT | TCG | GCC | CTC | TTG | GAG | GAC | CCC | GTG | GGG | ACG | GTG | 864 |
| Glu | Asp | Pro | Glu | Asp | Ser | Ala | Leu | Leu | Glu | Asp | Pro | Val | Gly | Thr | Val | |
| | | | | 275 | | | | | 280 | | | | | 285 | | |
| GCG | CCG | CAA | AGG | AAG | ATC | TTC | CAG | GAC | GCC | GCG | ACG | CCT | TAC | CAT | CAT | 912 |
| Ala | Pro | Gln | Arg | Lys | Ile | Phe | Gln | Asp | Ala | Ala | Thr | Pro | Tyr | His | His | |
| | | | 290 | | | | | 295 | | | | | 300 | | | |
| CAT | CAT | CAT | CAT | TAA | | | | | | | | | | | | 927 |
| His | His | His | His | | | | | | | | | | | | | |
| | | | 305 | | | | | | | | | | | | | |

( 2 ) INFORMATION FOR SEQ ID NO:2:

( i ) SEQUENCE CHARACTERISTICS:
        ( A ) LENGTH: 308 amino acids
        ( B ) TYPE: amino acid ( D ) TOPOLOGY: linear ( i i ) MOLECULE TYPE: protein ( x i ) SEQUENCE DESCRIPTION: SEQ ID NO:2:

| Asp | Pro | Lys | Tyr | Ala | Leu | Ala | Asp | Ala | Ser | Leu | Lys | Met | Ala | Asp | Pro |
|---|---|---|---|---|---|---|---|---|---|---|---|---|---|---|---|
| -2 | | 1 | | | 5 | | | | | 10 | | | | | |

| Asn | Arg | Phe | Arg | Gly | Lys | Asp | Leu | Pro | Val | Leu | Asp | Gln | Leu | Thr | Asp |
|---|---|---|---|---|---|---|---|---|---|---|---|---|---|---|---|
| 15 | | | | | 20 | | | | 25 | | | | | | 30 |

| Pro | Pro | Gly | Val | Arg | Arg | Val | Tyr | His | Ile | Gln | Ala | Gly | Leu | Pro | Asp |
|---|---|---|---|---|---|---|---|---|---|---|---|---|---|---|---|
| | | | | 35 | | | | | 40 | | | | | 45 | |

| Pro | Phe | Gln | Pro | Pro | Ser | Leu | Pro | Ile | Thr | Val | Tyr | Tyr | Ala | Val | Leu |
|---|---|---|---|---|---|---|---|---|---|---|---|---|---|---|---|
| | | | 50 | | | | | 55 | | | | | 60 | | |

| Glu | Arg | Ala | Cys | Arg | Ser | Val | Leu | Leu | Asn | Ala | Pro | Ser | Glu | Ala | Pro |
|---|---|---|---|---|---|---|---|---|---|---|---|---|---|---|---|
| | | 65 | | | | | 70 | | | | | 75 | | | |

| Gln | Ile | Val | Arg | Gly | Ala | Ser | Glu | Asp | Val | Arg | Lys | Gln | Pro | Tyr | Asn |
|---|---|---|---|---|---|---|---|---|---|---|---|---|---|---|---|
| | 80 | | | | | 85 | | | | | 90 | | | | |

| Leu | Thr | Ile | Ala | Trp | Phe | Arg | Met | Gly | Gly | Asn | Cys | Ala | Ile | Pro | Ile |
|---|---|---|---|---|---|---|---|---|---|---|---|---|---|---|---|
| 95 | | | | | 100 | | | | | 105 | | | | | 110 |

| Thr | Val | Met | Glu | Tyr | Thr | Glu | Cys | Ser | Tyr | Asn | Lys | Ser | Leu | Gly | Ala |
|---|---|---|---|---|---|---|---|---|---|---|---|---|---|---|---|
| | | | | 115 | | | | | 120 | | | | | 125 | |

| Cys | Pro | Ile | Arg | Thr | Gln | Pro | Arg | Trp | Asn | Tyr | Tyr | Asp | Ser | Phe | Ser |
|---|---|---|---|---|---|---|---|---|---|---|---|---|---|---|---|
| | | | 130 | | | | | 135 | | | | | 140 | | |

| Ala | Val | Ser | Glu | Asp | Asn | Leu | Gly | Phe | Leu | Met | His | Ala | Pro | Ala | Phe |
|---|---|---|---|---|---|---|---|---|---|---|---|---|---|---|---|
| | | 145 | | | | | 150 | | | | | 155 | | | |

| Glu | Thr | Ala | Gly | Thr | Tyr | Leu | Arg | Leu | Val | Lys | Ile | Asn | Asp | Trp | Thr |
|---|---|---|---|---|---|---|---|---|---|---|---|---|---|---|---|
| | 160 | | | | | 165 | | | | | 170 | | | | |

| Glu | Ile | Thr | Gln | Phe | Ile | Leu | Glu | His | Arg | Ala | Lys | Gly | Ser | Cys | Lys |
|---|---|---|---|---|---|---|---|---|---|---|---|---|---|---|---|
| 175 | | | | | 180 | | | | | 185 | | | | | 190 |

| Tyr | Ala | Leu | Pro | Leu | Arg | Ile | Pro | Pro | Ser | Ala | Cys | Leu | Ser | Pro | Gln |
|---|---|---|---|---|---|---|---|---|---|---|---|---|---|---|---|
| | | | | 195 | | | | | 200 | | | | | 205 | |

| Ala | Tyr | Gln | Gln | Gly | Val | Thr | Val | Asp | Ser | Ile | Gly | Met | Leu | Pro | Arg |
|---|---|---|---|---|---|---|---|---|---|---|---|---|---|---|---|
| | | | 210 | | | | | 215 | | | | | 220 | | |

| Phe | Ile | Pro | Glu | Asn | Gln | Arg | Thr | Val | Ala | Val | Tyr | Ser | Leu | Lys | Ile |
|---|---|---|---|---|---|---|---|---|---|---|---|---|---|---|---|
| | | 225 | | | | | 230 | | | | | 235 | | | |

| Ala | Gly | Trp | His | Gly | Pro | Lys | Ala | Pro | Tyr | Thr | Ser | Thr | Leu | Leu | Pro |
|---|---|---|---|---|---|---|---|---|---|---|---|---|---|---|---|
| | 240 | | | | | 245 | | | | | 250 | | | | |

| Pro | Glu | Leu | Ser | Glu | Thr | Pro | Asn | Ala | Thr | Gln | Pro | Glu | Leu | Ala | Pro |
|---|---|---|---|---|---|---|---|---|---|---|---|---|---|---|---|
| 255 | | | | | 260 | | | | | 265 | | | | | 270 |

| Glu | Asp | Pro | Glu | Asp | Ser | Ala | Leu | Leu | Glu | Asp | Pro | Val | Gly | Thr | Val |
|---|---|---|---|---|---|---|---|---|---|---|---|---|---|---|---|
| | | | | 275 | | | | | 280 | | | | | 285 | |

| Ala | Pro | Gln | Arg | Lys | Ile | Phe | Gln | Asp | Ala | Ala | Thr | Pro | Tyr | His | His |
|---|---|---|---|---|---|---|---|---|---|---|---|---|---|---|---|
| | | | 290 | | | | | 295 | | | | | 300 | | |

| His | His | His | His |
|---|---|---|---|
| | | 305 | |

( 2 ) INFORMATION FOR SEQ ID NO:3:

( i ) SEQUENCE CHARACTERISTICS:
  ( A ) LENGTH: 1608 base pairs
  ( B ) TYPE: nucleic acid
  ( C ) STRANDEDNESS: single
  ( D ) TOPOLOGY: linear ( i i ) MOLECULE TYPE: DNA (genomic)

( i x ) FEATURE:
  ( A ) NAME/KEY: CDS
  ( B ) LOCATION: 241..1422

(ix) FEATURE:
    (A) NAME/KEY: mat_peptide
    (B) LOCATION: 316..1422

(xi) SEQUENCE DESCRIPTION: SEQ ID NO:3:

```
GTGGCCCCGG CCCCCAACAA AAATCACGGT AGCCCGGCCG TGTGACACTA TCGTCCATAC      60

CGACCACACC GACGAACCCC TAAGGGGGAG GGGCCATTTT ACGAGGAGGA GGGGTATAAC     120

AAAGTCTGTC TTTAAAAAGC AGGGGTTAGG GAGTTGTTCG GTCATAAGCT TCAGCGCGAA     180

CGACCAACTA CCCCGATCAT CAGTTATCCT TAAGGTCTCT TTTGTGTGGT GCGTTCCGGT     240
```

| | | | | | | | | | | | | | | | | |
|---|---|---|---|---|---|---|---|---|---|---|---|---|---|---|---|---|
| ATG | GGG | GGG | ACT | GCC | GCC | AGG | TTG | GGG | GCC | GTG | ATT | TTG | TTT | GTC | GTC | 288 |
| Met | Gly | Gly | Thr | Ala | Ala | Arg | Leu | Gly | Ala | Val | Ile | Leu | Phe | Val | Val | |
| -25 | | | | -20 | | | | -15 | | | | -10 | | | | |
| ATA | GTG | GGC | CTC | CAT | GGG | GTC | CGC | GGC | AAA | TAT | GCC | TTG | GCG | GAT | GCC | 336 |
| Ile | Val | Gly | Leu | His | Gly | Val | Arg | Gly | Lys | Tyr | Ala | Leu | Ala | Asp | Ala | |
| | | | | -5 | | | | | 1 | | | | 5 | | | |
| TCT | CTC | AAG | ATG | GCC | GAC | CCC | AAT | CGC | TTT | CGC | GGC | AAA | GAC | CTT | CCG | 384 |
| Ser | Leu | Lys | Met | Ala | Asp | Pro | Asn | Arg | Phe | Arg | Gly | Lys | Asp | Leu | Pro | |
| | | 10 | | | | | 15 | | | | | 20 | | | | |
| GTC | CTG | GAC | CAG | CTG | ACC | GAC | CCT | CCG | GGG | GTC | CGG | CGC | GTG | TAC | CAC | 432 |
| Val | Leu | Asp | Gln | Leu | Thr | Asp | Pro | Pro | Gly | Val | Arg | Arg | Val | Tyr | His | |
| | | 25 | | | | 30 | | | | | 35 | | | | | |
| ATC | CAG | GCG | GGC | CTA | CCG | GAC | CCG | TTC | CAG | CCC | CCC | AGC | CTC | CCG | ATC | 480 |
| Ile | Gln | Ala | Gly | Leu | Pro | Asp | Pro | Phe | Gln | Pro | Pro | Ser | Leu | Pro | Ile | |
| 40 | | | | | 45 | | | | | 50 | | | | | 55 | |
| ACG | GTT | TAC | TAC | GCC | GTG | TTG | GAG | CGC | GCC | TGC | CGC | AGC | GTG | CTC | CTA | 528 |
| Thr | Val | Tyr | Tyr | Ala | Val | Leu | Glu | Arg | Ala | Cys | Arg | Ser | Val | Leu | Leu | |
| | | | | 60 | | | | | 65 | | | | | 70 | | |
| AAC | GCA | CCG | TCG | GAG | GCC | CCC | CAG | ATT | GTC | CGC | GGG | GCC | TCC | GAA | GAC | 576 |
| Asn | Ala | Pro | Ser | Glu | Ala | Pro | Gln | Ile | Val | Arg | Gly | Ala | Ser | Glu | Asp | |
| | | | 75 | | | | | 80 | | | | | 85 | | | |
| GTC | CGG | AAA | CAA | CCC | TAC | AAC | CTG | ACC | ATC | GCT | TGG | TTT | CGG | ATG | GGA | 624 |
| Val | Arg | Lys | Gln | Pro | Tyr | Asn | Leu | Thr | Ile | Ala | Trp | Phe | Arg | Met | Gly | |
| | | 90 | | | | | 95 | | | | | 100 | | | | |
| GGC | AAC | TGT | GCT | ATC | CCC | ATC | ACG | GTC | ATG | GAG | TAC | ACC | GAA | TGC | TCC | 672 |
| Gly | Asn | Cys | Ala | Ile | Pro | Ile | Thr | Val | Met | Glu | Tyr | Thr | Glu | Cys | Ser | |
| | | 105 | | | | | 110 | | | | | 115 | | | | |
| TAC | AAC | AAG | TCT | CTG | GGG | GCC | TGT | CCC | ATC | CGA | ACG | CAG | CCC | CGC | TGG | 720 |
| Tyr | Asn | Lys | Ser | Leu | Gly | Ala | Cys | Pro | Ile | Arg | Thr | Gln | Pro | Arg | Trp | |
| 120 | | | | | 125 | | | | | 130 | | | | | 135 | |
| AAC | TAC | TAT | GAC | AGC | TTC | AGC | GCC | GTC | AGC | GAG | GAT | AAC | CTG | GGG | TTC | 768 |
| Asn | Tyr | Tyr | Asp | Ser | Phe | Ser | Ala | Val | Ser | Glu | Asp | Asn | Leu | Gly | Phe | |
| | | | | 140 | | | | | 145 | | | | | 150 | | |
| CTG | ATG | CAC | GCC | CCC | GCG | TTT | GAG | ACC | GCC | GGC | ACG | TAC | CTG | CGG | CTC | 816 |
| Leu | Met | His | Ala | Pro | Ala | Phe | Glu | Thr | Ala | Gly | Thr | Tyr | Leu | Arg | Leu | |
| | | | 155 | | | | | 160 | | | | | 165 | | | |
| GTG | AAG | ATA | AAC | GAC | TGG | ACG | GAG | ATT | ACA | CAG | TTT | ATC | CTG | GAG | CAC | 864 |
| Val | Lys | Ile | Asn | Asp | Trp | Thr | Glu | Ile | Thr | Gln | Phe | Ile | Leu | Glu | His | |
| | | 170 | | | | | 175 | | | | | 180 | | | | |
| CGA | GCC | AAG | GGC | TCC | TGT | AAG | TAC | GCC | CTC | CCG | CTG | CGC | ATC | CCC | CCG | 912 |
| Arg | Ala | Lys | Gly | Ser | Cys | Lys | Tyr | Ala | Leu | Pro | Leu | Arg | Ile | Pro | Pro | |
| | | 185 | | | | | 190 | | | | | 195 | | | | |
| TCA | GCC | TGC | CTC | TCC | CCC | CAG | GCC | TAC | CAG | CAG | GGG | GTG | ACG | GTG | GAC | 960 |
| Ser | Ala | Cys | Leu | Ser | Pro | Gln | Ala | Tyr | Gln | Gln | Gly | Val | Thr | Val | Asp | |
| 200 | | | | | 205 | | | | | 210 | | | | | 215 | |
| AGC | ATC | GGG | ATG | CTG | CCC | CGC | TTC | ATC | CCC | GAG | AAC | CAG | CGC | ACC | GTC | 1008 |
| Ser | Ile | Gly | Met | Leu | Pro | Arg | Phe | Ile | Pro | Glu | Asn | Gln | Arg | Thr | Val | |
| | | | | 220 | | | | | 225 | | | | | 230 | | |
| GCC | GTA | TAC | AGC | TTG | AAG | ATC | GCC | GGG | TGG | CAC | GGG | CCC | AAG | GCC | CCA | 1056 |

|  |  |  |  |  |  |  |  |  |  |  |  |  |  |  |
|---|---|---|---|---|---|---|---|---|---|---|---|---|---|---|
| Ala | Val | Tyr | Ser | Leu | Lys | Ile | Ala | Gly | Trp | His | Gly | Pro | Lys | Ala | Pro |
|  |  |  | 235 |  |  |  | 240 |  |  |  |  | 245 |  |  |  |

```
TAC ACG AGC ACC CTG CTG CCC CCG GAG CTG TCC GAG ACC CCC AAC GCC    1104
Tyr Thr Ser Thr Leu Leu Pro Pro Glu Leu Ser Glu Thr Pro Asn Ala
        250             255             260

ACG CAG CCA GAA CTC GCC CCG GAA GAC CCC GAG GAT TCG GCC CTC TTG    1152
Thr Gln Pro Glu Leu Ala Pro Glu Asp Pro Glu Asp Ser Ala Leu Leu
    265             270             275

GAG GAC CCC GTG GGG ACG GTG GCG CCG CAA ATC CCA CCA AAC TGG CAC    1200
Glu Asp Pro Val Gly Thr Val Ala Pro Gln Ile Pro Pro Asn Trp His
280             285             290             295

ATC CCG TCG ATC CAG GAC GCC GCG ACG CCT TAC CAT CCC CCG GCC ACC    1248
Ile Pro Ser Ile Gln Asp Ala Ala Thr Pro Tyr His Pro Pro Ala Thr
            300             305             310

CCG AAC AAC ATG GGC CTG ATC GCC GGC GCG GTG GGC GGC AGT CTC CTG    1296
Pro Asn Asn Met Gly Leu Ile Ala Gly Ala Val Gly Gly Ser Leu Leu
        315             320             325

GCA GCC CTG GTC ATT TGC GGA ATT GTG TAC TGG ATG CAC CGC CGC ACT    1344
Ala Ala Leu Val Ile Cys Gly Ile Val Tyr Trp Met His Arg Arg Thr
        330             335             340

CGG AAA GCC CCA AAG CGC ATA CGC CTC CCC CAC ATC CGG GAA GAC GAC    1392
Arg Lys Ala Pro Lys Arg Ile Arg Leu Pro His Ile Arg Glu Asp Asp
345             350             355

CAG CCG TCC TCG CAC CAG CCC TTG TTT TAC TAGATACCCC CCCTTAATGG      1442
Gln Pro Ser Ser His Gln Pro Leu Phe Tyr
360             365

GTGCGGGGGG GTCAGGTCTG CGGGGTTGGG ATGGGACCTT AACTCCATAT AAAGCGAGTC  1502

TGGAAGGGGG GAAAGGCGGA CAGTCGATAA GTCGGTAGCG GGGACGCGC ACCTGTTCCG   1562

CCTGTCGCAC CCACAGCTTT TTCGCGAACC GTCCGTTTT CGGGAT                  1608
```

(2) INFORMATION FOR SEQ ID NO:4:

(i) SEQUENCE CHARACTERISTICS:
    (A) LENGTH: 394 amino acids
    (B) TYPE: amino acid
    (D) TOPOLOGY: linear (ii) MOLECULE TYPE: protein (xi) SEQUENCE DESCRIPTION: SEQ ID NO:4:

```
Met Gly Gly Thr Ala Ala Arg Leu Gly Ala Val Ile Leu Phe Val Val
-25             -20             -15             -10

Ile Val Gly Leu His Gly Val Arg Gly Lys Tyr Ala Leu Ala Asp Ala
            -5              1               5

Ser Leu Lys Met Ala Asp Pro Asn Arg Phe Arg Gly Lys Asp Leu Pro
        10              15              20

Val Leu Asp Gln Leu Thr Asp Pro Pro Gly Val Arg Arg Val Tyr His
    25              30              35

Ile Gln Ala Gly Leu Pro Asp Pro Phe Gln Pro Pro Ser Leu Pro Ile
40              45              50              55

Thr Val Tyr Tyr Ala Val Leu Glu Arg Ala Cys Arg Ser Val Leu Leu
            60              65              70

Asn Ala Pro Ser Glu Ala Pro Gln Ile Val Arg Gly Ala Ser Glu Asp
        75              80              85

Val Arg Lys Gln Pro Tyr Asn Leu Thr Ile Ala Trp Phe Arg Met Gly
    90              95              100

Gly Asn Cys Ala Ile Pro Ile Thr Val Met Glu Tyr Thr Glu Cys Ser
105             110             115
```

| | | | | | | | | | | | | | | |
|---|---|---|---|---|---|---|---|---|---|---|---|---|---|---|
| Tyr<br>120 | Asn | Lys | Ser | Leu | Gly<br>125 | Ala | Cys | Pro | Ile<br>130 | Arg | Thr | Gln | Pro | Arg<br>135 | Trp |
| Asn | Tyr | Tyr | Asp | Ser<br>140 | Phe | Ser | Ala | Val | Ser<br>145 | Glu | Asp | Asn | Leu<br>150 | Gly | Phe |
| Leu | Met | His | Ala<br>155 | Pro | Ala | Phe | Glu | Thr<br>160 | Ala | Gly | Thr | Tyr | Leu<br>165 | Arg | Leu |
| Val | Lys | Ile<br>170 | Asn | Asp | Trp | Thr | Glu<br>175 | Ile | Thr | Gln | Phe | Ile<br>180 | Leu | Glu | His |
| Arg | Ala<br>185 | Lys | Gly | Ser | Cys | Lys<br>190 | Tyr | Ala | Leu | Pro | Leu<br>195 | Arg | Ile | Pro | Pro |
| Ser<br>200 | Ala | Cys | Leu | Ser | Pro<br>205 | Gln | Ala | Tyr | Gln | Gln<br>210 | Gly | Val | Thr | Val | Asp<br>215 |
| Ser | Ile | Gly | Met | Leu<br>220 | Pro | Arg | Phe | Ile | Pro<br>225 | Glu | Asn | Gln | Arg | Thr<br>230 | Val |
| Ala | Val | Tyr | Ser<br>235 | Leu | Lys | Ile | Ala | Gly<br>240 | Trp | His | Gly | Pro | Lys<br>245 | Ala | Pro |
| Tyr | Thr | Ser<br>250 | Thr | Leu | Leu | Pro | Pro<br>255 | Glu | Leu | Ser | Glu | Thr<br>260 | Pro | Asn | Ala |
| Thr | Gln<br>265 | Pro | Glu | Leu | Ala | Pro<br>270 | Glu | Asp | Pro | Glu | Asp<br>275 | Ser | Ala | Leu | Leu |
| Glu<br>280 | Asp | Pro | Val | Gly | Thr<br>285 | Val | Ala | Pro | Gln | Ile<br>290 | Pro | Pro | Asn | Trp | His<br>295 |
| Ile | Pro | Ser | Ile | Gln<br>300 | Asp | Ala | Ala | Thr | Pro<br>305 | Tyr | His | Pro | Pro | Ala<br>310 | Thr |
| Pro | Asn | Asn | Met<br>315 | Gly | Leu | Ile | Ala | Gly<br>320 | Ala | Val | Gly | Gly | Ser<br>325 | Leu | Leu |
| Ala | Ala | Leu<br>330 | Val | Ile | Cys | Gly | Ile<br>335 | Val | Tyr | Trp | Met | His<br>340 | Arg | Arg | Thr |
| Arg | Lys<br>345 | Ala | Pro | Lys | Arg | Ile<br>350 | Arg | Leu | Pro | His | Ile<br>355 | Arg | Glu | Asp | Asp |
| Gln<br>360 | Pro | Ser | Ser | His | Gln<br>365 | Pro | Leu | Phe | Tyr | | | | | | |

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AGTTTGGTGG GAGGAAGATC TTCCTTTGCG GCGCCAC    37

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CCCAAGCTTA TCCTTAAGGT CTCTTT    26

(2) INFORMATION FOR SEQ ID NO:7:

( i ) SEQUENCE CHARACTERISTICS:
   ( A ) LENGTH: 37 base pairs
   ( B ) TYPE: nucleic acid
   ( C ) STRANDEDNESS: single
   ( D ) TOPOLOGY: linear ( i i ) MOLECULE TYPE: DNA ( x i ) SEQUENCE DESCRIPTION: SEQ ID NO:7:

TCGCGGCGTC CTGGAAGATC TTCCGGATCG ACGGGAT            37

( 2 ) INFORMATION FOR SEQ ID NO:8:

( i ) SEQUENCE CHARACTERISTICS:
      ( A ) LENGTH: 29 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:8:

GAAGATCTTC CGAGAACCAG CGCACCGTC                     29

( 2 ) INFORMATION FOR SEQ ID NO:9:

( i ) SEQUENCE CHARACTERISTICS:
      ( A ) LENGTH: 27 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:9:

CCCAAGCTTC CCGCAGACCT GACCCCC                       27

( 2 ) INFORMATION FOR SEQ ID NO:10:

( i ) SEQUENCE CHARACTERISTICS:
      ( A ) LENGTH: 1550 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 241..1404

( i x ) FEATURE:
      ( A ) NAME/KEY: mat_peptide
      ( B ) LOCATION: 316..1404

( x i ) SEQUENCE DESCRIPTION: SEQ ID NO:10:

GTGGCCCCGG CCCCCAACAA AAATCACGGT AGCCCGGCCG TGTGACACTA TCGTCCATAC    60

CGACCACACC GACGAACCCC TAAGGGGGAG GGGCCATTTT ACGAGGAGGA GGGGTATAAC   120

AAAGTCTGTC TTTAAAAAGC AGGGGTTAGG GAGTTGTTCG GTCATAAGCT TCAGCGCGAA   180

CGACCAACTA CCCCGATCAT CAGTTATCCT TAAGGTCTCT TTTGTGTGGT GCGTTCCGGT   240

ATG GGG GGG ACT GCC GCC AGG TTG GGG GCC GTG ATT TTG TTT GTC GTC    288
Met Gly Gly Thr Ala Ala Arg Leu Gly Ala Val Ile Leu Phe Val Val
-25            -20                 -15                 -10

ATA GTG GGC CTC CAT GGG GTC CGC GGC AAA TAT GCC TTG GCG GAT GCC    336
Ile Val Gly Leu His Gly Val Arg Gly Lys Tyr Ala Leu Ala Asp Ala
           -5                  1                   5

| | | | | | | | | | | | | | | | | |
|---|---|---|---|---|---|---|---|---|---|---|---|---|---|---|---|---|
| TCT | CTC | AAG | ATG | GCC | GAC | CCC | AAT | CGC | TTT | CGC | GGC | AAA | GAC | CTT | CCG | 384 |
| Ser | Leu | Lys | Met | Ala | Asp | Pro | Asn | Arg | Phe | Arg | Gly | Lys | Asp | Leu | Pro | |
| | | 10 | | | | | 15 | | | | | 20 | | | | |
| GTC | CTG | GAC | CAG | CTG | ACC | GAC | CCT | CCG | GGG | GTC | CGG | CGC | GTG | TAC | CAC | 432 |
| Val | Leu | Asp | Gln | Leu | Thr | Asp | Pro | Pro | Gly | Val | Arg | Arg | Val | Tyr | His | |
| | 25 | | | | | 30 | | | | | 35 | | | | | |
| ATC | CAG | GCG | GGC | CTA | CCG | GAC | CCG | TTC | CAG | CCC | CCC | AGC | CTC | CCG | ATC | 480 |
| Ile | Gln | Ala | Gly | Leu | Pro | Asp | Pro | Phe | Gln | Pro | Pro | Ser | Leu | Pro | Ile | |
| 40 | | | | | 45 | | | | | 50 | | | | | 55 | |
| ACG | GTT | TAC | TAC | GCC | GTG | TTG | GAG | CGC | GCC | TGC | CGC | AGC | GTG | CTC | CTA | 528 |
| Thr | Val | Tyr | Tyr | Ala | Val | Leu | Glu | Arg | Ala | Cys | Arg | Ser | Val | Leu | Leu | |
| | | | | 60 | | | | | 65 | | | | | 70 | | |
| AAC | GCA | CCG | TCG | GAG | GCC | CCC | CAG | ATT | GTC | CGC | GGG | GCC | TCC | GAA | GAC | 576 |
| Asn | Ala | Pro | Ser | Glu | Ala | Pro | Gln | Ile | Val | Arg | Gly | Ala | Ser | Glu | Asp | |
| | | | 75 | | | | | 80 | | | | | 85 | | | |
| GTC | CGG | AAA | CAA | CCC | TAC | AAC | CTG | ACC | ATC | GCT | TGG | TTT | CGG | ATG | GGA | 624 |
| Val | Arg | Lys | Gln | Pro | Tyr | Asn | Leu | Thr | Ile | Ala | Trp | Phe | Arg | Met | Gly | |
| | | 90 | | | | | 95 | | | | | 100 | | | | |
| GGC | AAC | TGT | GCT | ATC | CCC | ATC | ACG | GTC | ATG | GAG | TAC | ACC | GAA | TGC | TCC | 672 |
| Gly | Asn | Cys | Ala | Ile | Pro | Ile | Thr | Val | Met | Glu | Tyr | Thr | Glu | Cys | Ser | |
| | 105 | | | | | 110 | | | | | 115 | | | | | |
| TAC | AAC | AAG | TCT | CTG | GGG | GCC | TGT | CCC | ATC | CGA | ACG | CAG | CCC | CGC | TGG | 720 |
| Tyr | Asn | Lys | Ser | Leu | Gly | Ala | Cys | Pro | Ile | Arg | Thr | Gln | Pro | Arg | Trp | |
| 120 | | | | | 125 | | | | | 130 | | | | | 135 | |
| AAC | TAC | TAT | GAC | AGC | TTC | AGC | GCC | GTC | AGC | GAG | GAT | AAC | CTG | GGG | TTC | 768 |
| Asn | Tyr | Tyr | Asp | Ser | Phe | Ser | Ala | Val | Ser | Glu | Asp | Asn | Leu | Gly | Phe | |
| | | | | 140 | | | | | 145 | | | | | 150 | | |
| CTG | ATG | CAC | GCC | CCC | GCG | TTT | GAG | ACC | GCC | GGC | ACG | TAC | CTG | CGG | CTC | 816 |
| Leu | Met | His | Ala | Pro | Ala | Phe | Glu | Thr | Ala | Gly | Thr | Tyr | Leu | Arg | Leu | |
| | | 155 | | | | | 160 | | | | | 165 | | | | |
| GTG | AAG | ATA | AAC | GAC | TGG | ACG | GAG | ATT | ACA | CAG | TTT | ATC | CTG | GAG | CAC | 864 |
| Val | Lys | Ile | Asn | Asp | Trp | Thr | Glu | Ile | Thr | Gln | Phe | Ile | Leu | Glu | His | |
| | 170 | | | | | 175 | | | | | 180 | | | | | |
| CGA | GCC | AAG | GGC | TCC | TGT | AAG | TAC | GCC | CTC | CCG | CTG | CGC | ATC | CCC | CCG | 912 |
| Arg | Ala | Lys | Gly | Ser | Cys | Lys | Tyr | Ala | Leu | Pro | Leu | Arg | Ile | Pro | Pro | |
| 185 | | | | | 190 | | | | | 195 | | | | | | |
| TCA | GCC | TGC | CTC | TCC | CCC | CAG | GCC | TAC | CAG | CAG | GGG | GTG | ACG | GTG | GAC | 960 |
| Ser | Ala | Cys | Leu | Ser | Pro | Gln | Ala | Tyr | Gln | Gln | Gly | Val | Thr | Val | Asp | |
| 200 | | | | | 205 | | | | | 210 | | | | | 215 | |
| AGC | ATC | GGG | ATG | CTG | CCC | CGC | TTC | ATC | CCC | GAG | AAC | CAG | CGC | ACC | GTC | 1008 |
| Ser | Ile | Gly | Met | Leu | Pro | Arg | Phe | Ile | Pro | Glu | Asn | Gln | Arg | Thr | Val | |
| | | | | 220 | | | | | 225 | | | | | 230 | | |
| GCC | GTA | TAC | AGC | TTG | AAG | ATC | GCC | GGG | TGG | CAC | GGG | CCC | AAG | GCC | CCA | 1056 |
| Ala | Val | Tyr | Ser | Leu | Lys | Ile | Ala | Gly | Trp | His | Gly | Pro | Lys | Ala | Pro | |
| | | | 235 | | | | | 240 | | | | | 245 | | | |
| TAC | ACG | AGC | ACC | CTG | CTG | CCC | CCG | GAG | CTG | TCC | GAG | ACC | CCC | AAC | GCC | 1104 |
| Tyr | Thr | Ser | Thr | Leu | Leu | Pro | Pro | Glu | Leu | Ser | Glu | Thr | Pro | Asn | Ala | |
| | | 250 | | | | | 255 | | | | | 260 | | | | |
| ACG | CAG | CCA | GAA | CTC | GCC | CCG | GAA | GAC | CCC | GAG | GAT | TCG | GCC | CTC | TTG | 1152 |
| Thr | Gln | Pro | Glu | Leu | Ala | Pro | Glu | Asp | Pro | Glu | Asp | Ser | Ala | Leu | Leu | |
| | 265 | | | | | 270 | | | | | 275 | | | | | |
| GAG | GAC | CCC | GTG | GGG | ACG | GTG | GCG | CCG | CAA | AGG | AAG | ATC | TTC | CAG | GAC | 1200 |
| Glu | Asp | Pro | Val | Gly | Thr | Val | Ala | Pro | Gln | Arg | Lys | Ile | Phe | Gln | Asp | |
| 280 | | | | | 285 | | | | | 290 | | | | | 295 | |
| GCC | GCG | ACG | CCT | TAC | CAT | CCC | CCG | GCC | ACC | CCG | AAC | AAC | ATG | GGC | CTG | 1248 |
| Ala | Ala | Thr | Pro | Tyr | His | Pro | Pro | Ala | Thr | Pro | Asn | Asn | Met | Gly | Leu | |
| | | | | 300 | | | | | 305 | | | | | 310 | | |
| ATC | GCC | GGC | GCG | GTG | GGC | GGC | AGT | CTC | CTG | GCA | GCC | CTG | GTC | ATT | TGC | 1296 |
| Ile | Ala | Gly | Ala | Val | Gly | Gly | Ser | Leu | Leu | Ala | Ala | Leu | Val | Ile | Cys | |
| | | | 315 | | | | | 320 | | | | | 325 | | | |

| GGA | ATT | GTG | TAC | TGG | ATG | CAC | CGC | CGC | ACT | CGG | AAA | GCC | CCA | AAG | CGC | 1344 |
| Gly | Ile | Val | Tyr | Trp | Met | His | Arg | Arg | Thr | Arg | Lys | Ala | Pro | Lys | Arg | |
| | | 330 | | | | 335 | | | | | 340 | | | | | |

| ATA | CGC | CTC | CCC | CAC | ATC | CGG | GAA | GAC | GAC | CAG | CCG | TCC | TCG | CAC | CAG | 1392 |
| Ile | Arg | Leu | Pro | His | Ile | Arg | Glu | Asp | Asp | Gln | Pro | Ser | Ser | His | Gln | |
| 345 | | | | | 350 | | | | | 355 | | | | | | |

| CCC | TTG | TTT | TAC | TAGATACCCC | CCCTTAATGG | GTGCGGGGGG | GTCAGGTCTG | 1444 |
| Pro | Leu | Phe | Tyr | | | | | |
| 360 | | | | | | | | |

CGGGGTTGGG ATGGGACCTT AACTCCATAT AAAGCGAGTC TGGAAGGGGG GAAAGGCGGA         1504

CAGTCGATAA GTCGGTAGCG GGGACGCGC ACCTGTTCCG CCTGTC                          1550

( 2 ) INFORMATION FOR SEQ ID NO:11:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

| Met | Gly | Gly | Thr | Ala | Ala | Arg | Leu | Gly | Ala | Val | Ile | Leu | Phe | Val | Val |
| -25 | | | | | -20 | | | | | -15 | | | | | -10 |
| Ile | Val | Gly | Leu | His | Gly | Val | Arg | Gly | Lys | Tyr | Ala | Leu | Ala | Asp | Ala |
| | | | | -5 | | | | | 1 | | | | 5 | | |
| Ser | Leu | Lys | Met | Ala | Asp | Pro | Asn | Arg | Phe | Arg | Gly | Lys | Asp | Leu | Pro |
| | | 10 | | | | | 15 | | | | | 20 | | | |
| Val | Leu | Asp | Gln | Leu | Thr | Asp | Pro | Pro | Gly | Val | Arg | Arg | Val | Tyr | His |
| | | 25 | | | | | 30 | | | | | 35 | | | |
| Ile | Gln | Ala | Gly | Leu | Pro | Asp | Pro | Phe | Gln | Pro | Pro | Ser | Leu | Pro | Ile |
| 40 | | | | | 45 | | | | | 50 | | | | | 55 |
| Thr | Val | Tyr | Tyr | Ala | Val | Leu | Glu | Arg | Ala | Cys | Arg | Ser | Val | Leu | Leu |
| | | | | 60 | | | | | 65 | | | | | 70 | |
| Asn | Ala | Pro | Ser | Glu | Ala | Pro | Gln | Ile | Val | Arg | Gly | Ala | Ser | Glu | Asp |
| | | | 75 | | | | | 80 | | | | | 85 | | |
| Val | Arg | Lys | Gln | Pro | Tyr | Asn | Leu | Thr | Ile | Ala | Trp | Phe | Arg | Met | Gly |
| | | | 90 | | | | | 95 | | | | | 100 | | |
| Gly | Asn | Cys | Ala | Ile | Pro | Ile | Thr | Val | Met | Glu | Tyr | Thr | Glu | Cys | Ser |
| | | 105 | | | | | 110 | | | | | 115 | | | |
| Tyr | Asn | Lys | Ser | Leu | Gly | Ala | Cys | Pro | Ile | Arg | Thr | Gln | Pro | Arg | Trp |
| 120 | | | | | 125 | | | | | 130 | | | | | 135 |
| Asn | Tyr | Tyr | Asp | Ser | Phe | Ser | Ala | Val | Ser | Glu | Asp | Asn | Leu | Gly | Phe |
| | | | | 140 | | | | | 145 | | | | | 150 | |
| Leu | Met | His | Ala | Pro | Ala | Phe | Glu | Thr | Ala | Gly | Thr | Tyr | Leu | Arg | Leu |
| | | | 155 | | | | | 160 | | | | | 165 | | |
| Val | Lys | Ile | Asn | Asp | Trp | Thr | Glu | Ile | Thr | Gln | Phe | Ile | Leu | Glu | His |
| | | | 170 | | | | | 175 | | | | | 180 | | |
| Arg | Ala | Lys | Gly | Ser | Cys | Lys | Tyr | Ala | Leu | Pro | Leu | Arg | Ile | Pro | Pro |
| | | 185 | | | | | 190 | | | | | 195 | | | |
| Ser | Ala | Cys | Leu | Ser | Pro | Gln | Ala | Tyr | Gln | Gln | Gly | Val | Thr | Val | Asp |
| 200 | | | | | 205 | | | | | 210 | | | | | 215 |
| Ser | Ile | Gly | Met | Leu | Pro | Arg | Phe | Ile | Pro | Glu | Asn | Gln | Arg | Thr | Val |
| | | | | 220 | | | | | 225 | | | | | 230 | |
| Ala | Val | Tyr | Ser | Leu | Lys | Ile | Ala | Gly | Trp | His | Gly | Pro | Lys | Ala | Pro |
| | | | 235 | | | | | 240 | | | | | 245 | | |
| Tyr | Thr | Ser | Thr | Leu | Leu | Pro | Pro | Glu | Leu | Ser | Glu | Thr | Pro | Asn | Ala |

|  | 250 |  |  |  | 255 |  |  |  | 260 |  |  |  |
|---|---|---|---|---|---|---|---|---|---|---|---|---|
| Thr | Gln | Pro | Glu | Leu | Ala | Pro | Glu | Asp | Pro | Glu | Asp | Ser | Ala | Leu | Leu |
|  | 265 |  |  |  | 270 |  |  |  | 275 |  |  |  |

| Glu | Asp | Pro | Val | Gly | Thr | Val | Ala | Pro | Gln | Arg | Lys | Ile | Phe | Gln | Asp |
| 280 |  |  |  |  | 285 |  |  |  | 290 |  |  |  |  |  | 295 |

| Ala | Ala | Thr | Pro | Tyr | His | Pro | Pro | Ala | Thr | Pro | Asn | Asn | Met | Gly | Leu |
|  |  |  |  | 300 |  |  |  |  | 305 |  |  |  |  | 310 |  |

| Ile | Ala | Gly | Ala | Val | Gly | Gly | Ser | Leu | Leu | Ala | Ala | Leu | Val | Ile | Cys |
|  |  |  | 315 |  |  |  |  | 320 |  |  |  |  | 325 |  |  |

| Gly | Ile | Val | Tyr | Trp | Met | His | Arg | Arg | Thr | Arg | Lys | Ala | Pro | Lys | Arg |
|  |  | 330 |  |  |  |  | 335 |  |  |  |  | 340 |  |  |  |

| Ile | Arg | Leu | Pro | His | Ile | Arg | Glu | Asp | Asp | Gln | Pro | Ser | Ser | His | Gln |
|  | 345 |  |  |  |  | 350 |  |  |  |  | 355 |  |  |  |  |

| Pro | Leu | Phe | Tyr |
| 360 |  |  |  |

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TTTTGGATCC CAAATATGCC TTGGCGGATG         30

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGCGCTGCGG AATGGTAGTA GTAGTAGTAA TTGACGTCTT TT         42

(2) INFORMATION FOR SEQ ID NO:14:

(i) SEQUENCE CHARACTERISTICS:
        (A) LENGTH: 1635 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 268..1446

(ix) FEATURE:
        (A) NAME/KEY: mat_peptide
        (B) LOCATION: 343..1446

(xi) SEQUENCE DESCRIPTION: SEQ ID NO:14:

CTTGGGGGGG GGGGGGAAGA AACTAAAAAC ACATCAAGCC CACAACCCAT CCCACAAGGG     60

GGGTTATGGC GGACCCACCG CACCACCATA CTCCGATTCG ACCACATATG CAACCAAATC    120

ACCCCCAGAG GGGAGGTTCC ATTTTTACGA GGAGGAGGAG TATAATAGAG TCTTTGTGTT    180

-continued

```
TAAAACCCGG GGTCGGTGTG GTGTTCGGTC ATAAGCTGCA TTGCGAACCA CTAGTCGCCG        240

TTTTTCGTGT GCATCGCGTA TCACGGC ATG GGG CGT TTG ACC TCC GGC GTC            291
                              Met Gly Arg Leu Thr Ser Gly Val
                              -25                 -20

GGG ACG GCG GCC CTG CTA GTT GTC GCG GTG GGA CTC CGC GTC GTC TGC          339
Gly Thr Ala Ala Leu Leu Val Val Ala Val Gly Leu Arg Val Val Cys
        -15             -10                         -5

GCC AAA TAC GCC TTA GCA GAC CCC TCG CTT AAG ATG GCC GAT CCC AAT          387
Ala Lys Tyr Ala Leu Ala Asp Pro Ser Leu Lys Met Ala Asp Pro Asn
    1           5                   10                      15

CGA TTT CGC GGG AAG AAC CTT CCG GTT TTG GAC CAG CTG ACC GAC CCC          435
Arg Phe Arg Gly Lys Asn Leu Pro Val Leu Asp Gln Leu Thr Asp Pro
                20              25                  30

CCC GGG GTG AAG CGT GTT TAC CAC ATT CAG CCG AGC CTG GAG GAC CCG          483
Pro Gly Val Lys Arg Val Tyr His Ile Gln Pro Ser Leu Glu Asp Pro
            35                  40                  45

TTC CAG CCC CCC AGC ATC CCG ATC ACT GTG TAC TAC GCA GTG CTG GAA          531
Phe Gln Pro Pro Ser Ile Pro Ile Thr Val Tyr Tyr Ala Val Leu Glu
        50                  55                  60

CGT GCC TGC CAC AGC GTG CTC CTA CAT GCC CCA TCG GAG GCC CCC CAG          579
Arg Ala Cys His Ser Val Leu Leu His Ala Pro Ser Glu Ala Pro Gln
    65                  70                  75

ATC GTG CGC GGG GCT TCG GAC GAG GCC CGA AAG CAC ACG TAC AAC CTG          627
Ile Val Arg Gly Ala Ser Asp Glu Ala Arg Lys His Thr Tyr Asn Leu
80                  85                  90                  95

ACC ATC GCC TGG TAT CGC ATG GGA GAC AAT TGC GCT ATC CCC ATC ACG          675
Thr Ile Ala Trp Tyr Arg Met Gly Asp Asn Cys Ala Ile Pro Ile Thr
                100                 105                 110

GTC ATG GAG TAC ACC GAG TGC CCC TAC AAC AAG TCT TTG GGG GTC TGC          723
Val Met Glu Tyr Thr Glu Cys Pro Tyr Asn Lys Ser Leu Gly Val Cys
            115                 120                 125

CCC ATC CGA ACG CAG CCC CGC TGG AGC TAC TAT GAC AGC TTT AGC GCC          771
Pro Ile Arg Thr Gln Pro Arg Trp Ser Tyr Tyr Asp Ser Phe Ser Ala
        130                 135                 140

GTC AGC GAG GAT AAC CTG GGA TTC CTG ATG CAC GCC CCC GCG TTC GAG          819
Val Ser Glu Asp Asn Leu Gly Phe Leu Met His Ala Pro Ala Phe Glu
145                 150                 155

ACC GCG GGT ACG TAC CTG CGG CTA GTG AAG ATA AAC GAC TGG ACG GAG          867
Thr Ala Gly Thr Tyr Leu Arg Leu Val Lys Ile Asn Asp Trp Thr Glu
160                 165                 170                 175

ATC ACA CAA TTT ATC CTG GAG CAC CGG GCC CGC GCC TCC TGC AAG TAC          915
Ile Thr Gln Phe Ile Leu Glu His Arg Ala Arg Ala Ser Cys Lys Tyr
                180                 185                 190

GCT CTC CCC CTG CGC ATC CCC CCG GCA GCG TGC CTC ACC TCG AAG GCC          963
Ala Leu Pro Leu Arg Ile Pro Pro Ala Ala Cys Leu Thr Ser Lys Ala
            195                 200                 205

TAC CAA CAG GGC GTG ACG GTC GAC AGC ATC GGG ATG CTC CCC CGC TTT         1011
Tyr Gln Gln Gly Val Thr Val Asp Ser Ile Gly Met Leu Pro Arg Phe
        210                 215                 220

ATC CCC GAA AAC CAG CGC ACC GTC GCC CTA TAC AGC TTA AAA ATC GCC         1059
Ile Pro Glu Asn Gln Arg Thr Val Ala Leu Tyr Ser Leu Lys Ile Ala
225                 230                 235

GGG TGG CAC GGC CCC AAG CCC CCG TAC ACC AGC ACC CTG CTG CCG CCG         1107
Gly Trp His Gly Pro Lys Pro Pro Tyr Thr Ser Thr Leu Leu Pro Pro
240                 245                 250                 255

GAG CTG TCC GAC ACC ACC AAC GCC ACG CAA CCC GAA CTC GTT CCG GAA         1155
Glu Leu Ser Asp Thr Thr Asn Ala Thr Gln Pro Glu Leu Val Pro Glu
                260                 265                 270

GAC CCC GAG GAC TCG GCC CTC TTA GAG GAT CCC GCC GGG ACG GTG TCT         1203
```

|  |  |  |  |  |  |  |  |  |  |  |  |  |  |  |  |
|---|---|---|---|---|---|---|---|---|---|---|---|---|---|---|---|
| Asp | Pro | Glu | Asp<br>275 | Ser | Ala | Leu | Leu | Glu<br>280 | Asp | Pro | Ala | Gly | Thr<br>285 | Val | Ser |

| TCG | CAG | ATC | CCC | CCA | AAC | TGG | CAC | ATC | CCG | TCG | ATC | CAG | GAC | GTC | GCG | 1251 |
|---|---|---|---|---|---|---|---|---|---|---|---|---|---|---|---|---|
| Ser | Gln | Ile<br>290 | Pro | Pro | Asn | Trp | His<br>295 | Ile | Pro | Ser | Ile | Gln<br>300 | Asp | Val | Ala |  |

| CCG | CAC | CAC | GCC | CCC | GCC | GCC | CCC | AGC | AAC | CCG | GGC | CTG | ATC | ATC | GGC | 1299 |
|---|---|---|---|---|---|---|---|---|---|---|---|---|---|---|---|---|
| Pro | His<br>305 | His | Ala | Pro | Ala | Ala<br>310 | Pro | Ser | Asn | Pro | Gly<br>315 | Leu | Ile | Ile | Gly |  |

| GCG | CTG | GCC | GGC | AGT | ACC | CTG | GCG | GCG | CTG | GTC | ATC | GGC | GGT | ATT | GCG | 1347 |
|---|---|---|---|---|---|---|---|---|---|---|---|---|---|---|---|---|
| Ala<br>320 | Leu | Ala | Gly | Ser | Thr<br>325 | Leu | Ala | Ala | Leu | Val<br>330 | Ile | Gly | Gly | Ile | Ala<br>335 |  |

| TTT | TGG | GTA | CGC | CGC | CGC | GCT | CAG | ATG | GCC | CCC | AAG | CGC | CTA | CGT | CTC | 1395 |
|---|---|---|---|---|---|---|---|---|---|---|---|---|---|---|---|---|
| Phe | Trp | Val | Arg | Arg<br>340 | Arg | Ala | Gln | Met | Ala<br>345 | Pro | Lys | Arg | Leu | Arg<br>350 | Leu |  |

| CCC | CAC | ATC | CGG | GAT | GAC | GAC | GCG | CCC | CCC | TCG | CAC | CAG | CCA | TTG | TTT | 1443 |
|---|---|---|---|---|---|---|---|---|---|---|---|---|---|---|---|---|
| Pro | His | Ile | Arg<br>355 | Asp | Asp | Asp | Ala | Pro<br>360 | Pro | Ser | His | Gln | Pro<br>365 | Leu | Phe |  |

| TAC | TAGAGGAGTT | TCCCCGTTCC | CGTGTACCTC | TGGGCCCGTG | TGGGAGGGTG | 1496 |
|---|---|---|---|---|---|---|
| Tyr |  |  |  |  |  |  |

| GCCGGGGTAT | TTGGGTGGGA | CTTGGACTCC | GCATAAAGGG | AGTCTCGAAG | GAGGGAAACT | 1556 |
|---|---|---|---|---|---|---|
| AGGACAGTTC | ATAGGCCGGG | AGCGTGGGGC | GCGCACCGCG | TCCCGACGAT | TAGCCACCGC | 1616 |
| GCCCACAGCC | ACCTCGACC |  |  |  |  | 1635 |

(2) INFORMATION FOR SEQ ID NO:15:

(i) SEQUENCE CHARACTERISTICS:
        (A) LENGTH: 393 amino acids
        (B) TYPE: amino acid
        (D) TOPOLOGY: linear (ii) MOLECULE TYPE: protein (xi) SEQUENCE DESCRIPTION: SEQ ID NO:15:

| Met<br>-25 | Gly | Arg | Leu | Thr | Ser<br>-20 | Gly | Val | Gly | Thr | Ala<br>-15 | Ala | Leu | Leu | Val | Val<br>-10 |
|---|---|---|---|---|---|---|---|---|---|---|---|---|---|---|---|
| Ala | Val | Gly | Leu | Arg<br>-5 | Val | Val | Cys | Ala | Lys<br>1 | Tyr | Ala | Leu | Ala<br>5 | Asp | Pro |
| Ser | Leu | Lys<br>10 | Met | Ala | Asp | Pro | Asn<br>15 | Arg | Phe | Arg | Gly | Lys<br>20 | Asn | Leu | Pro |
| Val | Leu<br>25 | Asp | Gln | Leu | Thr | Asp<br>30 | Pro | Pro | Gly | Val | Lys<br>35 | Arg | Val | Tyr | His |
| Ile<br>40 | Gln | Pro | Ser | Leu | Glu<br>45 | Asp | Pro | Phe | Gln | Pro<br>50 | Pro | Ser | Ile | Pro | Ile<br>55 |
| Thr | Val | Tyr | Tyr | Ala<br>60 | Val | Leu | Glu | Arg | Ala<br>65 | Cys | His | Ser | Val | Leu<br>70 | Leu |
| His | Ala | Pro | Ser<br>75 | Glu | Ala | Pro | Gln | Ile<br>80 | Val | Arg | Gly | Ala | Ser<br>85 | Asp | Glu |
| Ala | Arg | Lys<br>90 | His | Thr | Tyr | Asn | Leu<br>95 | Thr | Ile | Ala | Trp | Tyr<br>100 | Arg | Met | Gly |
| Asp | Asn<br>105 | Cys | Ala | Ile | Pro | Ile<br>110 | Thr | Val | Met | Glu | Tyr<br>115 | Thr | Glu | Cys | Pro |
| Tyr | Asn | Lys | Ser | Leu | Gly<br>125 | Val | Cys | Pro | Ile | Arg<br>130 | Thr | Gln | Pro | Arg | Trp<br>135 |
| 120 |  |  |  |  |  |  |  |  |  |  |  |  |  |  |  |
| Ser | Tyr | Tyr | Asp | Ser<br>140 | Phe | Ser | Ala | Val | Ser<br>145 | Glu | Asp | Asn | Leu | Gly<br>150 | Phe |
| Leu | Met | His<br>155 | Ala | Pro | Ala | Phe | Glu<br>160 | Thr | Ala | Gly | Thr | Tyr<br>165 | Leu | Arg | Leu |

-continued

| | | | | | | | | | | | | | | |
|---|---|---|---|---|---|---|---|---|---|---|---|---|---|---|
| Val | Lys | Ile 170 | Asn | Asp | Trp | Thr | Glu 175 | Ile | Thr | Gln | Phe | Ile 180 | Leu | Glu | His |
| Arg | Ala 185 | Arg | Ala | Ser | Cys | Lys 190 | Tyr | Ala | Leu | Pro | Leu 195 | Arg | Ile | Pro | Pro |
| Ala 200 | Ala | Cys | Leu | Thr | Ser 205 | Lys | Ala | Tyr | Gln | Gln 210 | Gly | Val | Thr | Val | Asp 215 |
| Ser | Ile | Gly | Met | Leu 220 | Pro | Arg | Phe | Ile | Pro 225 | Glu | Asn | Gln | Arg | Thr 230 | Val |
| Ala | Leu | Tyr | Ser 235 | Leu | Lys | Ile | Ala | Gly 240 | Trp | His | Gly | Pro | Lys 245 | Pro | Pro |
| Tyr | Thr | Ser 250 | Thr | Leu | Leu | Pro | Pro 255 | Glu | Leu | Ser | Asp | Thr 260 | Thr | Asn | Ala |
| Thr | Gln 265 | Pro | Glu | Leu | Val | Pro 270 | Glu | Asp | Pro | Glu | Asp 275 | Ser | Ala | Leu | Leu |
| Glu 280 | Asp | Pro | Ala | Gly | Thr 285 | Val | Ser | Ser | Gln | Ile 290 | Pro | Pro | Asn | Trp | His 295 |
| Ile | Pro | Ser | Ile | Gln 300 | Asp | Val | Ala | Pro | His 305 | His | Ala | Pro | Ala | Ala 310 | Pro |
| Ser | Asn | Pro | Gly 315 | Leu | Ile | Ile | Gly | Ala 320 | Leu | Ala | Gly | Ser | Thr 325 | Leu | Ala |
| Ala | Leu | Val 330 | Ile | Gly | Gly | Ile | Ala 335 | Phe | Trp | Val | Arg | Arg 340 | Arg | Ala | Gln |
| Met | Ala 345 | Pro | Lys | Arg | Leu | Arg 350 | Leu | Pro | His | Ile | Arg 355 | Asp | Asp | Asp | Ala |
| Pro 360 | Pro | Ser | His | Gln | Pro 365 | Leu | Phe | Tyr | | | | | | | |

HERPES SIMPLEX VIRUS GLYCOPROTEIN D VARIANTS

FIELD OF THE INVENTION

The present invention relates generally to novel herpes simplex virus glycoprotein D molecules. More particularly, the present invention relates to variant glycoprotein D molecules which are capable of blocking infection of cells by herpes simplex virus.

BACKGROUND OF THE INVENTION

Herpes simplex viruses (HSV) are human pathogens which cause a variety of disease states including cold sores, eye and genital infections, life-threatening neonatal infections, and encephalitis. HSV is also capable of establishing latent infections in ganglia. The strains designated HSV-1 (oral) and HSV-2 (genital) are members of the family Herpesviridae and are classified in the subfamily alphahexpesvirinae and the genus simplex virus. The viruses have an enveloped double-stranded DNA genome of 150 kilobases (kb) including at least seventy-two open reading frames which encode at least eleven glycoproteins. The genomes of HSV-1 and HSV-2 exhibit extensive homology in regions which are known to encode proteins responsible for antigenic specificity and/or biological activity.

Upon infection, several vital glycoproteins act singly or in concert to bind HSV to a susceptible cell and trigger direct fusion between the virion envelope and the cell membrane. Glycoprotein D (gD) of HSV is a component of the virion envelope which plays an essential role in HSV entry into susceptible mammalian cells. The evidence to date suggests that gD binds to a cellular molecule, possibly the mannose-6-phosphate receptor, following the initial interaction of HSV glycoproteins gC and gB with heparan sulfate proteoglycans. The interaction between gD and its receptor may stabilize the virus-cell complex prior to membrane fusion which is mediated by other essential glycoproteins such as gB, gH, and gL. See Sisk et al., *J. Virol.*, 68(3): 766–775 (1994) and Tat-Singer et al., *J. Virol.*, 69(7): 4471–4483 (1995). The nucleotide sequence of the Patton strain of HSV-1 gD (gD-1) (SEQ ID NO: 3) was first reported in Watson et al., *Science*, 218:381–384 (1982). The strain 333 HSV-2 gD (gD-2) was described in Muggeridge et al., *J. Virol.*, 64(8): 3617–3626 (1990). The nucleotide sequence of the strain 333 gD-2 gene is set out in SEQ ID NO: 14 herein.

The HSV glycoproteins have been the subject of intense research in development of vaccines useful in preventing or treating HSV infections. See especially, U.S. Pat. Nos. 4,709,011 issued Nov. 24, 1987; 4,762,708 issued Aug. 9, 1988; and 5,149,660 issued Sep. 22, 1992; all to co-inventors herein. In addition, significant effort has been expended in the development of anti-vital agents such as nucleoside analogues and interferons. Nucleoside analogues idoxuridine, trifluridine, vidarabine and acyclovir interfere with HSV genome replication. Interferons interfere with the translation of vital proteins.

While some clinical benefit in ameliorating the sequelae of HSV infection has been achieved by treatment with nucleoside analogues and interferons, therapy with both types of compounds can involve significant side effects. See Fields and Knipe, Eds., *Fundamental Virology*, Chapter 16, Raven Press, New York, N.Y. (1986). Patients treated with acyclovir, for example, may exhibit local inflammation at silos where the drug is administered, renal dysfunction, and encephalopathic changes. Moreover, HSV mutants resistant to acyclovir have been observed and suppression of recurrences ceases when acyclovir is discontinued [Straus et al., *N. Eng. J. Med.*, 310:1545–1550 (1984)]. Experience in the use of vidarabine has revealed neurologic toxicity. Patients treated with interferon may exhibit fever, fatigue, anorexia, weight loss, nausea and vomiting, bone marrow suppression, pain at injection sites, lymphadenopathy, and mild hair loss. Fibroblast interferon has also been reported to induce the formation of anti-interferon antibodies.

There thus exists a need in the art for additional products useful in preventing or treating HSV infection.

SUMMARY OF THE INVENTION

The present invention provides variant HSV gD molecules capable of preventing infection of cells by HSV-1 and/or HSV-2. Also provided are novel purified and isolated polynucleotides (i.e., DNA and RNA both sense and antisense strands) encoding the variant gD molecules. HSV gD-1 and gD-2 region IV variants or fragments thereof are specifically contemplated by the invention.

Generally described, variant gD-1 and gD-2 molecules of the invention are subject to variation and amino acid sequence modification in "region IV" amino acid residues comprising amino acids 277 through 310 of the native Patton strain gD-1 sequence which are conserved, for example, as residues 276 through 309 of strain 333 gD-2. Modifications preferably include deletions of one or more amino acids at region IV amino acids 290–300 of gD-1 (residues 289 through 299 of gD-2) and most preferably the deletion of, e.g., gD-1 amino acids 290–299. One or more amino acid residues not normally present in region IV may replace one or more region IV residues deleted. It is also preferred that "transmembrane" region amino acid sequences ordinarily present in native gD-1 and gD-2 proteins be deleted, for example, by deletion of carboxy terminal residues 306–369 of gD-1 (305 through 368 of gD-2). The above-noted modifications do not operate to delete any of the native potential N-linked glycosylation sites of gD-1 and gD-2 polypeptides, so that recombinant expression of the molecules in host cells capable of glycosylation will ordinarily be expected to result in formation of glycoprotein products. Variant gD-1 and gD-2 proteins and glycoproteins of the invention, when produced by recombinant methods, may include additional amino acid residues as artifacts of the expression system employed (e.g., residues remaining after signal sequence processing of fusion proteins) or as a result of modification for purposes of facilitating protein/glycoprotein isolation (e.g., a polyhistidine carboxy terminal sequence).

The presently preferred gD-1 variant molecule, designated gD-1 (Δ290–299t), is the product of recombinant expression in Sf9 cells of a fusion protein including the signal peptide of honeybee melittin [Tessier et al., *Gene*, 98:177–183 (1991)] and Patton strain HSV-1 gD wherein (1) the Patton strain amino acid residues 290 through 299 of the mature gD-1 protein have been replaced with the amino acid residues arginine, lysine, isoleucine and phenylalanine, and (2) Patton strain amino acid residues 308 through 369 have been replaced with five histidine residues. When expressed in Sf9 cells, cleavage of the melittin signal peptide results in the presence of aspartate and proline residues at the amino terminus of the variant molecule. The amino acid sequence of gD-1(Δ290–299t) is set out in SEQ ID NO: 2 and the preferred DNA sequence encoding gD-1(Δ290–299t) is set out in SEQ ID NO: 1.

Also provided are full-length gD variants in which step (1) above is performed, but step (2) is not. The amino acid sequence of such a variant, designated gD-1 (Δ290–299) is set out in SEQ ID NO: 11 and the preferred DNA sequence encoding gD-1 (Δ290–299) is set out in SEQ ID NO: 10.

Autonomously replicating recombinant constructions such as plasmid and viral DNA vectors incorporating sequences encoding variant gD molecules and especially vectors wherein DNA encoding variant gD molecules is operatively linked to an endogenous or exogenous expression control DNA sequence and a transcription terminator are also provided.

According to another aspect of the invention, procaryotic or eucaryotic host cells are stably transformed with DNA sequences of the invention in a manner allowing the desired variant gD molecule or fragment thereof to be expressed therein. Host cells expressing variant gD molecules can serve a variety of useful purposes. Such cells constitute a valuable source of immunogen for the development of antibody substances specifically immunoreactive with the gD variants. Host cells of the invention are conspicuously useful in methods for the large scale production of variant gD molecules or fragments thereof wherein the cells are grown in a suitable culture medium and the desired pelypeptide products are isolated from the cells or from the medium in which the cells are grown by, for example, immunoaffinity purification or purification on nickel affinity columns.

HSV variant gD molecules may be chemically synthesized, but are preferably produced by recombinant procedures involving procaryotic or eucaryotic host cells of the invention. The use of insect (e.g., Sf9 cells) or mammalian host cells is expected to provide for such pest-translational modifications (e.g., myristolation, glycosylation, truncation, lipidation and tyrosine, serine or threonine phosphorylation) as may be needed to confer optimal biological activity on recombinant expression products of the invention.

Also comprehended by the present invention are antibody substances (e.g., monoclonal and polyclonal antibodies, single chain antibodies, chimefie murine variable region/ human constant region antibodies, CDR-grafted antibodies and the like) and other binding proteins specific for the variant gD molecules. Anti-idiotypic antibodies specific for the variant gD molecule-specific antibody substances are also contemplated. Antibody substances of the invention are conspicuously useful in purifying or detecting variant molecules of the invention.

Administration of gD variant molecules or fragments thereof to mammalian subjects, especially humans, for the purpose of preventing 1HSV infection and/or ameliorating pathological sequelae of HSV infection is specifically contemplated. Various animal models for HSV infection are accepted in the art and include, but are not limited to, the rabbit and mouse eye models of herpes keratitis [Hill et al., *Curr. Eye Res.*, 6:1065–1071 (1987) and Rock and Fraser, *Nature*, 302: 523–525 (1983)], cutaneous herpes infection of hairless (nude) mice [Metcalf et al., *Infect. Immunol.*, 26:1164–1171 (1979)], vaginal lesions in the guinea pig and mouse [Stanberry et al., *J. Infect. Dis.*, 146:397–404 (1982)], foot pad model in mice [Stevens and Cook, *Science*, 173:843–845 (1971)], zosterform skin model in mice [Hill et al., *J. Gen. Virol.*, 39:21–28 (1982)], and experimental herpes simplex encephalitis induced by intracerebral viral inoculation in mice [Tenser, *J. Infect. Dis.*, 147:956 (1983)]. For review, see Stevens, *Microbiol. Rev.*, 53:318–332 (1989) and Stanberry, *Current Topics in Microbiol. and Immunol.*, 179:15–30 (1992). The gD variant molecules are administered to the mammal in an amount sufficient to block infection of susceptible cells by HSV. Administration may be by intravenous, intramuscular, subcutaneous, oral, suppository, mucosal, or topical routes. Also contemplated is DNA immunization wherein DNA encoding a gD variant molecule of the invention is provided to a mammal.

Compositions of the invention, when administered intravenously, intramuscularly, or orally, are administered in quantities so that variant gD molecules are provided at unit doses of from 0.01 to 10.0 micrograms of gD variant molecule per kilogram of the recipients mammal's body weight. If administered orally or topically, compositions of the invention will include from about 0.0001% to 20% variant gD molecule. Compositions of the invention also include therapeutically acceptable carriers (e.g., diluents and/or adjuvants). For general dosage and formulation considerations see *Remmington's Pharmaceutical Sciences*, 18th Edition, Mack Publishing Co., Easton, Pa. (1990).

It is also contemplated that the HSV gD variant molecules may act as immunogens in a mammalian recipient when administered by systemic or mucosal routes. Immunization of animals With wild type gD stimulates the production of virus neutralizing antibodies and protects them from lethal challenge with HSV-1 and HSV-2 [Long et al., *Infect. Immunol.*, 37:761–764 (1984)]. The contemplated dual nature of the gD variant molecules is an advantage of the invention not shared by prior anti-HSV compounds discussed herein.

BRIEF DESCRIPTION OF THE DRAWINGS

Numerous other aspects and advantages of the present invention will be apparent to those skilled in the art upon consideration of the following detailed description of illustrative embodiments thereof, reference being made to the drawing wherein:

FIG. 2 is an alignment of wild type HSV gD-1 (SEQ ID NO: 4) and gD-2 (SEQ ID NO: 15) amino acid sequences;

FIGS. 4A to 4B are graphs depicting the inhibitory effect of gD-1(Δ290–299t) on plaque formation on Veto (FIG. 4A) and BHK (FIG. 4B) cells exposed to HSV;

FIG. 8 is a table summarizing the results of the plaque formation, cell to cell spread, and HSV entry assays of the invention for region IV variant gD-1 molecules of the invention.

DETAILED DESCRIPTION OF THE INVENTION

Figure 1A:
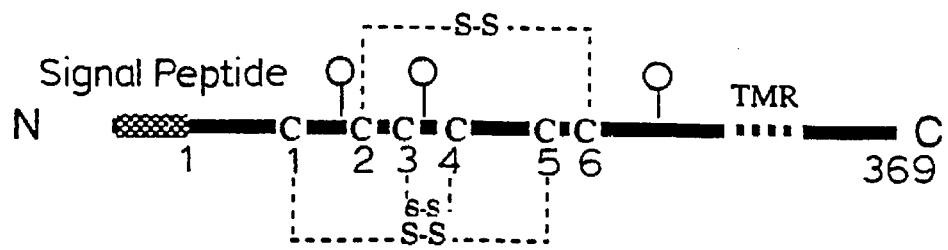
FIGS. 1A to 1C are schematic drawings of significant regions of full length wild type HSV gD-1, a carboxy terminal truncated wild type HSV gD-1 designated gD-1 (3061), and a region IV variant HSV gD-1 of the invention designated gD-1(Δ290–299t)

Numerous variant HSV-1 molecules were constructed and analyzed for the ability to rescue infectivity of the gD-null virus F-gD/β [Ligas and Johnson, *J. Virol.*, 62:1486–1494 (1988)]. Variant molecules with mutations in one of four regions of gD (region I comprising amino acid residues 27 through 43, region II comprising amino acid residues 126 through 161, region III comprising amino acid residues 225 through 246, and region IV comprising amino acid residues 277 through 310) were unable to effect rescue. The four regions of gD-1 were thus determined to be necessary for entry of HSV into susceptible cells. Further analysis of representative variant molecules, each including mutations in one of the regions, identified a region IV gD variant molecule with particularly potent anti-viral activity.

The following examples illustrate the invention wherein Example 1 describes the construction of vectors encoding variant gD-1 molecules of the invention, Example 2 describes recombinant expression of the variants in mammalian and insect cells, Example 3 presents results of analyses of the conformation of the variants and the ability of the variants to complement the null virus F-gDβ, and Example 4 presents results of analyses of the ability of the variants to bind HSV susceptible cells and to block infection of HSV-susceptible cells.

EXAMPLE 1

HSV gD-1 variants were constructed by linker-insertion mutagenesis essentially as described in Chiang et al., *J. Virol.*, 68(4): 2529–2543 (1994) which is incorporated by reference herein.

A gene encoding the region IV HSV gD-1 variant gD-1 (Δ290–299t) was constructed from the wild-type gD-1 gene as follows.

First, a plasmid pHC236 containing a 12-base BglII linker inserted at amino acid 290 of gD-1, was generated by oligonucleotide-directed mutagenesis [Kunkel et al., *Methods Enzymol.*, 154:367–382 (1988)]. The HindIII fragment containing the entire coding region of gD-1 was excised from plasmid pWW78 described in Muggeridge et al., supra, and then subcloned into the HindIII site of M13 mp18. The sequence of the Patton strain wild type gD-1 coding region present in the HindIII fragment is set out in SEQ ID NO: 3. A 37 base mutagenic oligonucleotide primer, 5'AGTTTGGTGGGAGGAAGATCTTCCTTTGCGGCGCCAC 3' (SEQ ID NO: 5) which corresponds to nucleotides 1171 to 1196 of SEQ ID NO: 3 and which contained a 12 bp BglII linker (underlined), was used to synthesize the replicative form (RF) of M13 mp18. The mutated gD-1 gene was then excised from RF DNA and inserted into the expression vector pRSVnt EPA (Chiang et al., supra) which contains the long terminal repeat of Rous sarcoma virus as a promoter and the SV40 early polyadenylation signal. The resulting construct designated pi-I236 encodes full-length gD-1 with the amino acid arginine replacing isoleucine at residue 290 and the amino acids lysine, isoleucine, phenylalanine, and leucine inserted after the arginine residue.

Second, a plasmid pHC237 containing a 12-base BglII linker inserted at amino acid 300 of gD-1 was constructed by a three-step PCR procedure. The 5' segment of the gD-1 gene was synthesized using a gD-1 upstream primer, 5'CCCAAGCTTATCCTTAAGGTCTCTTT 3'(SEQ ID NO: 6) which corresponds to nucleotides 206 to 223 of SEQ ID NO: 3 and which contains the recognition sequence for the restriction enzyme HindIII (underlined) to facilitate subsequent insertion into expression vector pRSVnt EPA, and an anti-sense strand primer, 5'TCGCGGCGTCCTGGAAGATCTTCCGGATCGACGGGAT 3' (SEQ ID NO: 7) which corresponds to nucleotides 1201 to 1225 of SEQ ID NO: 3 and which contains the BglIII linker (underlined). The primers were used to amplify gD-1 sequences from plasmid pRE4 [Cohen et al., *J. Virol.*, 62:1932–1940 (1988)]. The 3' segment of the gene was synthesized using a sense primer, 5'GAAGATCTTCCGAGAACCAGCGCACCGTC 3' (SEQ ID NO: 8) which corresponds to nucleotides 991 to 1008 of SEQ ID NO: 3, and a gD-1 downstream primer, 5'CCCAAGCTTCCCGCAGACCTGACCCCC 3' (SEQ ID NO: 9) which corresponds to nucleotides 1449 to 1466 of SEQ ID NO: 3 and which contains the recognition sequence for HindIII (underlined), to amplify sequences from template plasmid pRE4. In both cases, twenty-five cycles of amplification were performed; in each cycle the template was denatured at 94° C. for 1 minute, primers were then annealed to the template at 55° C. for 2 minutes, and the bound primers were extended at 72° C. for 3 minutes. The 5' and the 3' DNA segments were purified by electroelution. The segments were linked by an additional round of amplification wherein the gD-1 upstream and downstream primers and the 5' and the 3' segments as templates. The mutant DNA product was electroeluted, HindIII digested and ligated with pRSVnt EPA. The proper orientation of the insert was determined by restriction enzyme analysis. The resulting plasmid pHC237 encodes full length gD-1 with arginine, lysine, isoleucine, and phenylalanine residues inserted after amino acid 299.

Third, the BamHI-BglII fragment of pHC236 including 5' gD coding sequences was ligated to the BglII-BamHI fragment of pHC237 including 3' gD coding sequences to generate the plasmid pHC240. This plasmid encodes the variant gD molecule gD-1 (Δ290–299). The DNA and deduced amino acid sequences of gD-1(Δ290–299) are set out in SEQ ID NOs: 10 and 11, respectively.

Fourth, in a further variant of this molecule, the plasmid pHC240 was further engineered to produce the plasmid designated pAN258, which contains six histidine residues at its carboxy terminus and is soluble in an aqueous medium. Amino acid residues 300 through 306 of the wild-type gD-1 protein corresponded to amino acid residues 295–300 of the variant.

Thus, a soluble form of variant gD-1(Δ290–299) was generated by PCR using plasmid pHC240 as template. Primers 5'TTTTGGATCCCAAATATGCCTTGGCGGATG 3' (SEQ 112) NO: 12), which corresponds to nucleotides 316 to 334 of SEQ ID NO: 10 and contains a BamHI restriction site (underlined), and 5'GGCGCTGCGGAATGGTAGTAGTAGTAGTAATTGACGTCTTTT 3' (SEQ ID NO: 13), which corresponds to nucleotides 1202 to 1215 of SEQ ID NO: 10 and encodes a tyrosine residue and a six residue poly histidine tail (double underlined) and a PstI site (underlined), were used to truncate the encoded protein at amino acid 306 of SEQ ID NO: 11. Forty-five amplification cycles of 1 minute at 94° C., 30 seconds at 52° C., and 2 minutes at 75° C. were performed. The amplification products were examined on a 1% agarose gel and the desired fragment was purified from the gel. The fragment was then digested with BamHI and PstI and inserted into similarly digested plasmid pVTBac [Tressier et al., supra] for use in baculovirus expression. The plasmid pVTBac includes a melittin signal peptide and cleavage site (two residues upstream of the gD-1 mature protein initial lysine residue) to allow for secretion of the protein of interest from baculovirus-infected host cells. The resulting plasmid pAN258 encoded the region IV variant gD molecule with a carboxy-terminal truncation which was designated gD-1 (Δ290–299t). The DNA and deduced amino acid sequences of the variant are set out in SEQ ID NOs: 1 and 2, respectively.

Genes encoding full length and truncated region I, II, and III HSV gD-1 variant molecules were constructed by similar standard recombinant DNA methods. The full length variants were designated gD-1(∇34), gD-1(∇126), and gD-1 (∇243), respectively, and the truncated variants were designated gD-1(∇34t), gD-1(∇126t), and gD-1(∇243t), respectively. The full length and truncated variants gD-1 (∇34) and gD-1(∇34t) contained a glycine at position 34 instead of the valine residue at position 34 of wild type gD-1 and lysine, isoleucine, phenylalanine, and leucine residues inserted after the glycine; gD-1(∇126) and gD-1(∇126t) contained a glycine at position 126 instead of the alanine residue at position 126 of wild type gD-1 and contained lysine, isoleucine, phenylalanine and proline residues inserted after the glycine; and gD-1(∇243) and gD-1 (∇243t) contained a glycine residue at position 243 and contained glycine, arginine, serine, and serine residues inserted after the glycine. A gene encoding a secreted version of wild type gD-1 designated gD-1(306t) containing Patton strain gD-1 residues 1 through 307 and five additional histine residues at the carboxy terminus was also constructed to provide a soluble control protein.

Figure 1B:
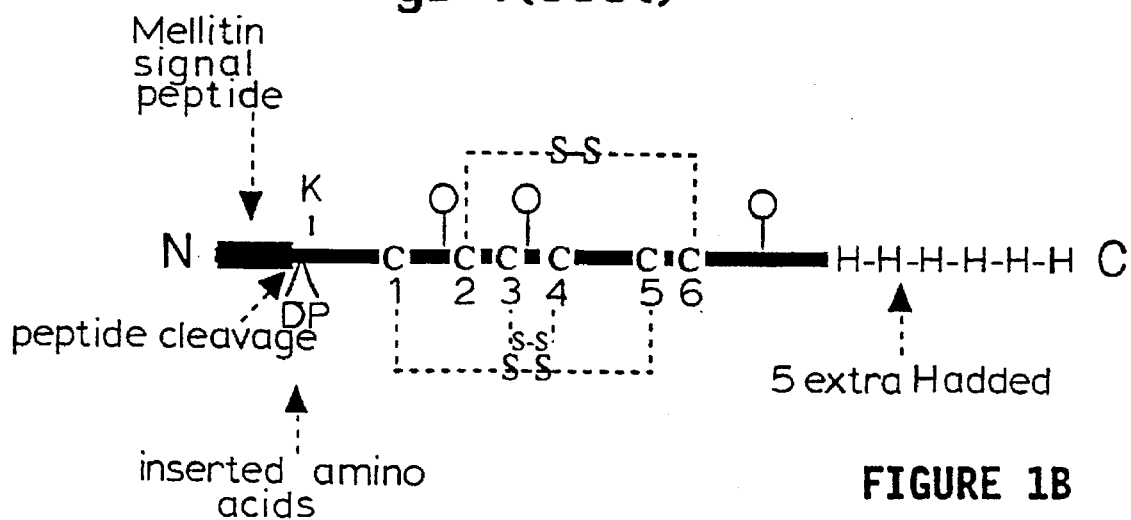
Figure 1C:
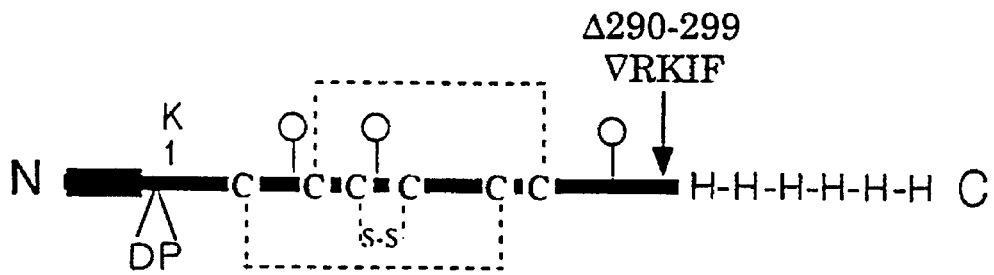

FIG. 1 is a schematic drawing which shows significant features of wild type gD-1 and variant gD-1(306t) and gD-1(Δ290–299t) molecules cysteine residues (c), disulfide bonds (S—S), and potential N-linked glycosylation sites.

EXAMPLE 2

Full length variant gD molecules were expressed in COS-1 or L cells transfected with the genes described in Example 1 by a modified calcium phosphate-DNA coprecipitation method described in Cohen et al., supra. Full-length variants may also be expressed using baculovirus vectors in Sf9 cells [Landolfi et al., Vaccine, 11: 407–414 (1993)].

Truncated variant gD molecules were expressed in Sf9 cells. pVTbac vectors containing the genes encoding the variants were cotransfected with wild type baculovirus DNA in the form of BaculoGold (Pharmingen, San Diego, Calif.) linear DNA into Sf9 cells. Cotransfection was mediated by cationic liposomes (Lipofectin, GIBCO, Grand Island, N.Y.) according to the manufacturer's specifications. Recombinant virus stocks were prepared essentially as described in Sisk et al., supra. To express the truncated variant gD molecules, suspension cultures of Sf9 cells were infected with one of the recombinant virus stocks, cells were pelleted and the medium containing the variant gD molecules was subjected to immunoaffinity chromatography on a DL-6 (produced by hybridoma ATCC HB 8606) IgG Sepharose column as described in Sisk et al., supra to purify the variants.

EXAMPLE 3

The structural and functional characteristics of the variant gD-1 molecules in comparison to wild type gD-1 were examined by various assays.

The structural integrity of the variants was assessed by measuring the ability of each variant to bind to monoclonal antibodies recognizing discontinuous gD-1 epitopes as a reflection of conformation; studying cell surface expression as a reflection of proper transport, and measuring protein aggregation as an indication of improper folding. The variants were also examined by circular dichroism.

Five monoclonal antibodies (AP7, HD1, DL11, ABD, and DL2) recognizing different gD-1 discontinuous epitopes [Chiang et al., supra and Muggeridge et al., Chapter 20 in van Regenmortel and Neurath, Eds., Immunochemistry of Viruses, II, The Basis for Serodiagnosis and Vaccines, Elsevier Science Publishers (1990)] were used to examine the antigenic conformation of the variants. Cytoplasmic extracts containing full length variants were prepared from COS-1 cells at 40 hours posttransfection and assayed for antibody binding by Western blot. Baculovirus-produced truncated region I, II, 1II, and IV variants were assayed for antibody binding by ELISA. Binding of the antibodies to the truncated variants was similar to that seen for the full length variant molecules. In each case, the variant proteins were still bound by one or more of the monoclonal antibodies which recognize conformational epitopes indicating that the conformation of the gD variants was not grossly altered by the mutations. The region IV variant was bound by all but monoclonal antibody AP7 indicating that its conformation was the most similar to wild type gD. Given the extensive homology between wild type gD-1 and gD-2 [see FIG. 2 which presents an alignment of the Patton strain gD-1 amino acid sequence (SEQ D NO: 4) and the strain 333 gD-2 amino acid sequence (SEQ ID NO: 15)], the invention specifically contemplates that region IV gD-2 variants which contain mutations corresponding to the gD-1 mutations described herein will have similar characteristics.

When examined by circular dichroism, the region II, 1/I, and IV variants [gD-1(∇126), gD-1(∇243), and gD-1 (Δ290–299t)] resembled gD-1(306t) in secondary structure, but the region I variant gD-1(∇34) differed in secondary structure.

Finally, to examine the functional characteristics of the variant gD-1 molecules, the ability of the variants to rescue the infectivity of the gD-null virus F-gDβ was assayed. The virus replicates in and forms plaques on VD60 cells which contain an integrated gD gene under the control of its own promoter. L cells transiently transfected with genes encoding a variant were then superinfected with F-gDβ. Pseudotype particles were harvested and litered on VD60 cells. The number of plaques measure the extent to which the variant gD molecule rescued the infectivity of the null virus. When infectivity was rescued with the wild type gD gene, the yields were typically $2 \times 10^6$ PFU of progeny extracellular virus and $10^6$ PFU of intracellular virus. Virus yields from wild-type gD were considered to be 100%. The region I, II, III, and IV variant gD-1 molecules were able to complement the null virus in some cases only at very low levels and in other cases not at all.

These experiments indicated that while mutations in regions I, II, III, and IV had minor effects on the conformation of the variant gD molecules, the mutations still had profound effects on the functional characteristics of the molecules.

EXAMPLE 4

Functional properties of the baculovirus-produced truncated variant gD molecules were examined further in cell binding and HSV blocking assays.

Binding of the variants to fixed Vero and BHK cells was measured by ELISA as described in Tat-Singer et al., supra. Truncated wild type gD-1(306t) and the truncated region I, II, III, and IV variant gD-1 molecules all bound to the fixed cells.

Figure 3A:
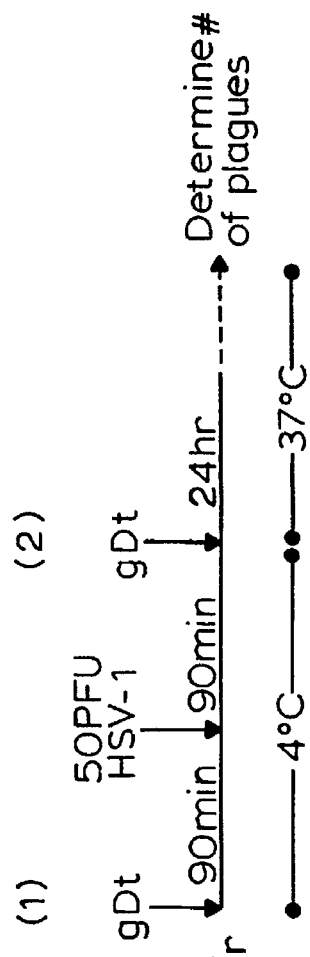
FIGS. 3A to 3C are schematic drawings of the steps in plaque formation (FIG. 3A), cell to cell spread (FIG. 3B) and virus blocking, HSV-1/lacZ+ entry (FIG. 3C) assays utilized in the examples.
Figure 3B:
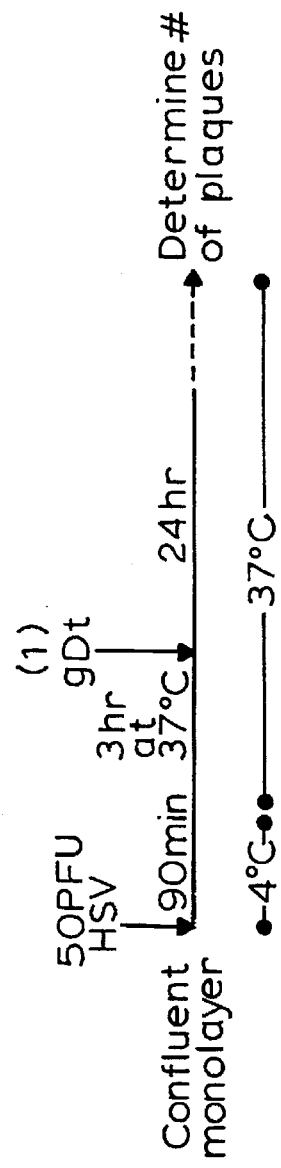
Figure 3C:
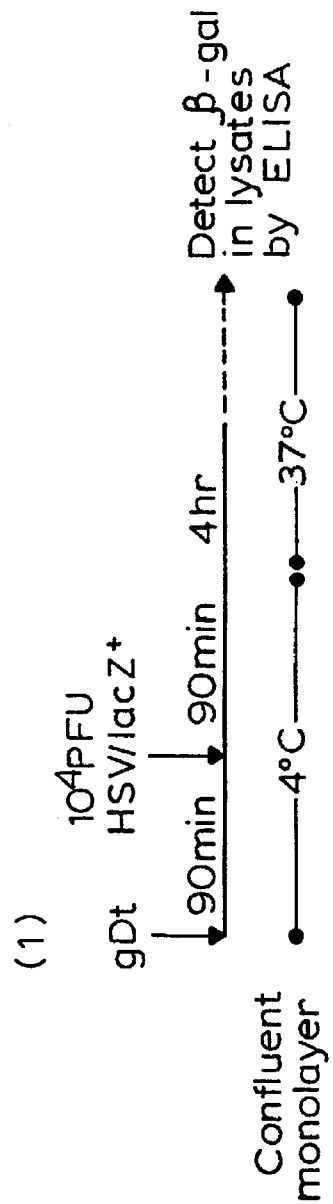

The ability of the variants to block HSV-1 infection of susceptible cells was measured by three assays diagrammed in FIG. 3, a plaque formation assay, a cell to cell spread assay, and an HSV-1/lacZ+ entry assay.

The plaque formation assays were performed as described in Tal-Singer et al., supra. Briefly Vero or BHK cell monolayers in 48-well plates were treated with region I, II, III, or IV variant or BSA diluted in 5% DMEM for 1.5 hours at 4° C. HSV-1 strain NS was added at 50 PFU per well for 1.5 hours and then treated with variant or BSA. After 24 hours at 37° C., the medium was removed and the cells were fixed and air dried. Virus liters were determined by immunoperoxidase assay and the mount of variant needed to block HSV infection was titrated. Results of the assays for the truncated wild type gD-1 molecule and the gD-1 (Δ290–299t) variant are presented in FIGS. 4A and 4B. If the amount of wild type gD-1(306t) needed to block infection by more than 60% is equal to 1, the region I variant gD-1(∇34t) failed to block infection at all, the region III variant gD-1(∇243t) blocked one-half as well as wild type, and the region II variant gD-1(∇126t) blocked as well as wild type. In comparison to these results, a significant increase in ability to block infection was exhibited by the region IV variant gD-1 (Δ290–299t). It was able to block infection about 400 times better than wild type gD-1.

Figure 5:
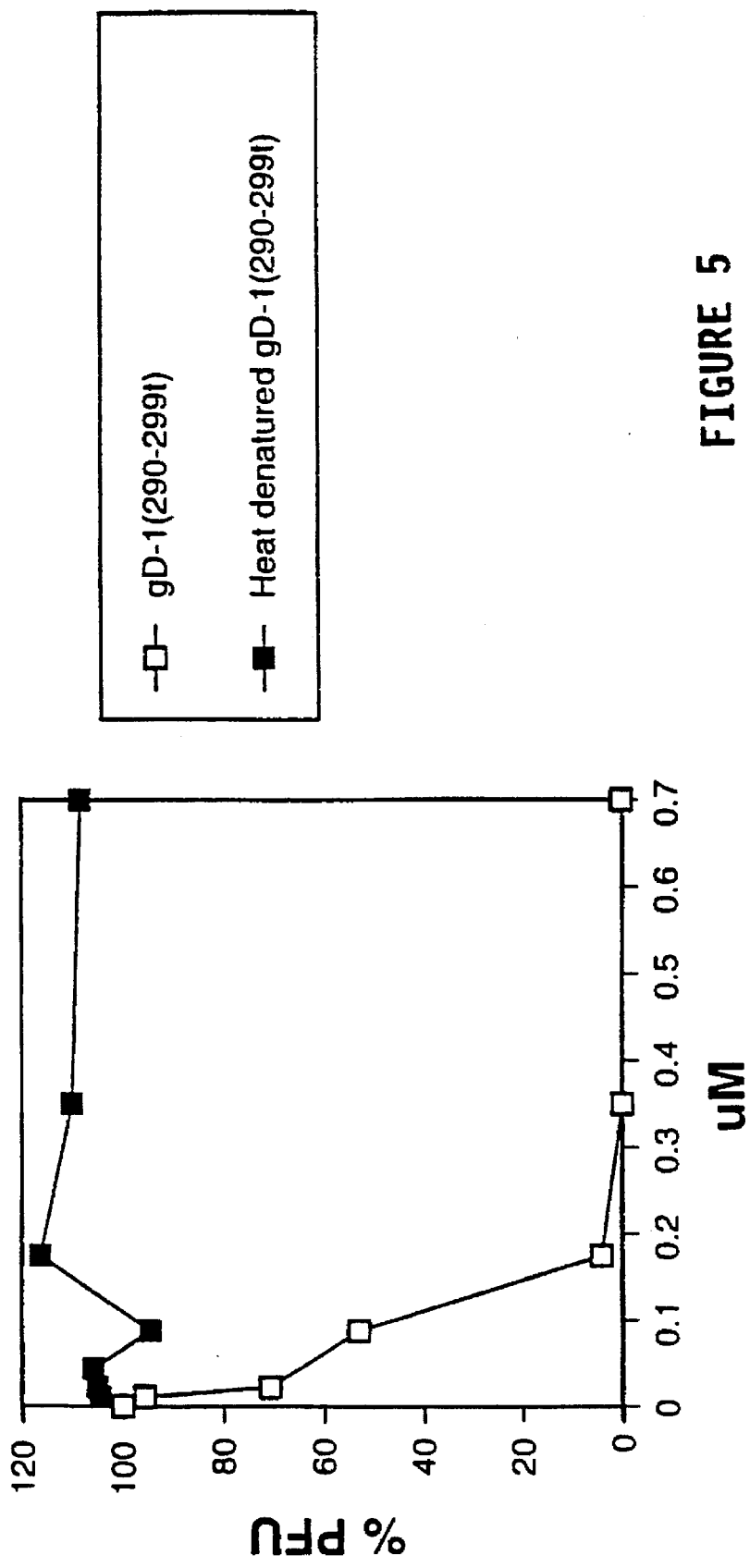
FIG. 5 is a graph depicting the effect of heat denaturation on the ability of gD-1(Δ290–299t) to block plaque formation on BHK cells exposed to HSV.

When variant gD-1(Δ290–299t) was denatured by heating to 65° C. for 5 minutes and then chilled to 4° C. before the plaque formation assay was performed, the variant was incapable of blocking HSV infection. Heat denaturation destroys secondary and tertiary structure of gD but leaves disulfide bonds intact. See FIG. 5.

The region IV variant gD-1(Δ290–299t) exhibited similar blocking effects in cell to cell spread and HSV/lacZ+ entry assays.

Figure 6:
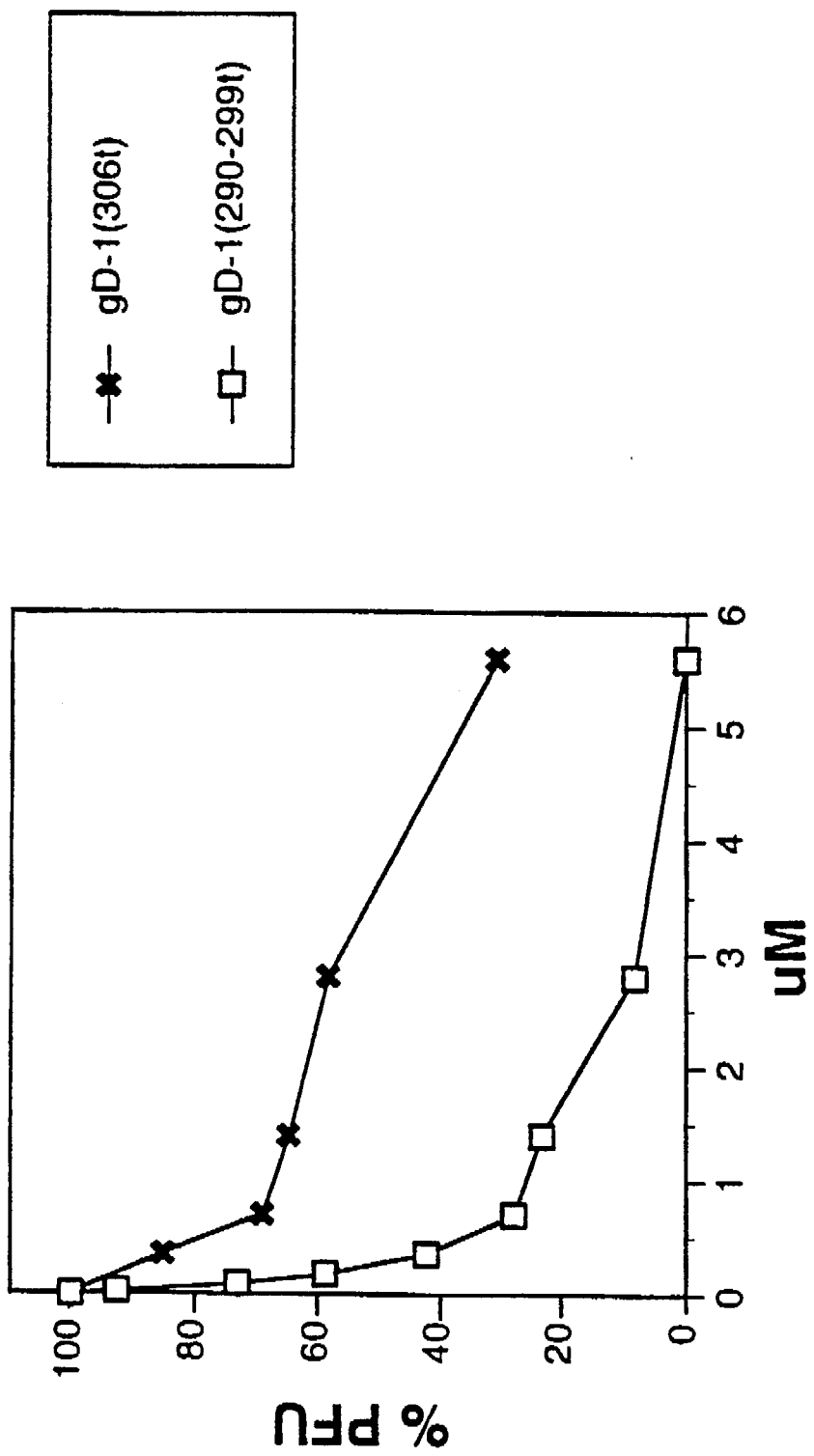
FIG. 6 is a graph illustrating the inhibitory effect of gD-1(Δ290–299t) on cell to cell spread of HSV in Vero cells.

The cell to cell spread assay was performed in the same manner as the plaque formation assay, except that the gD proteins were not added until 3 hours after cells were infected with HSV. Results of the assays are presented in FIG. 6.

Figure 7:
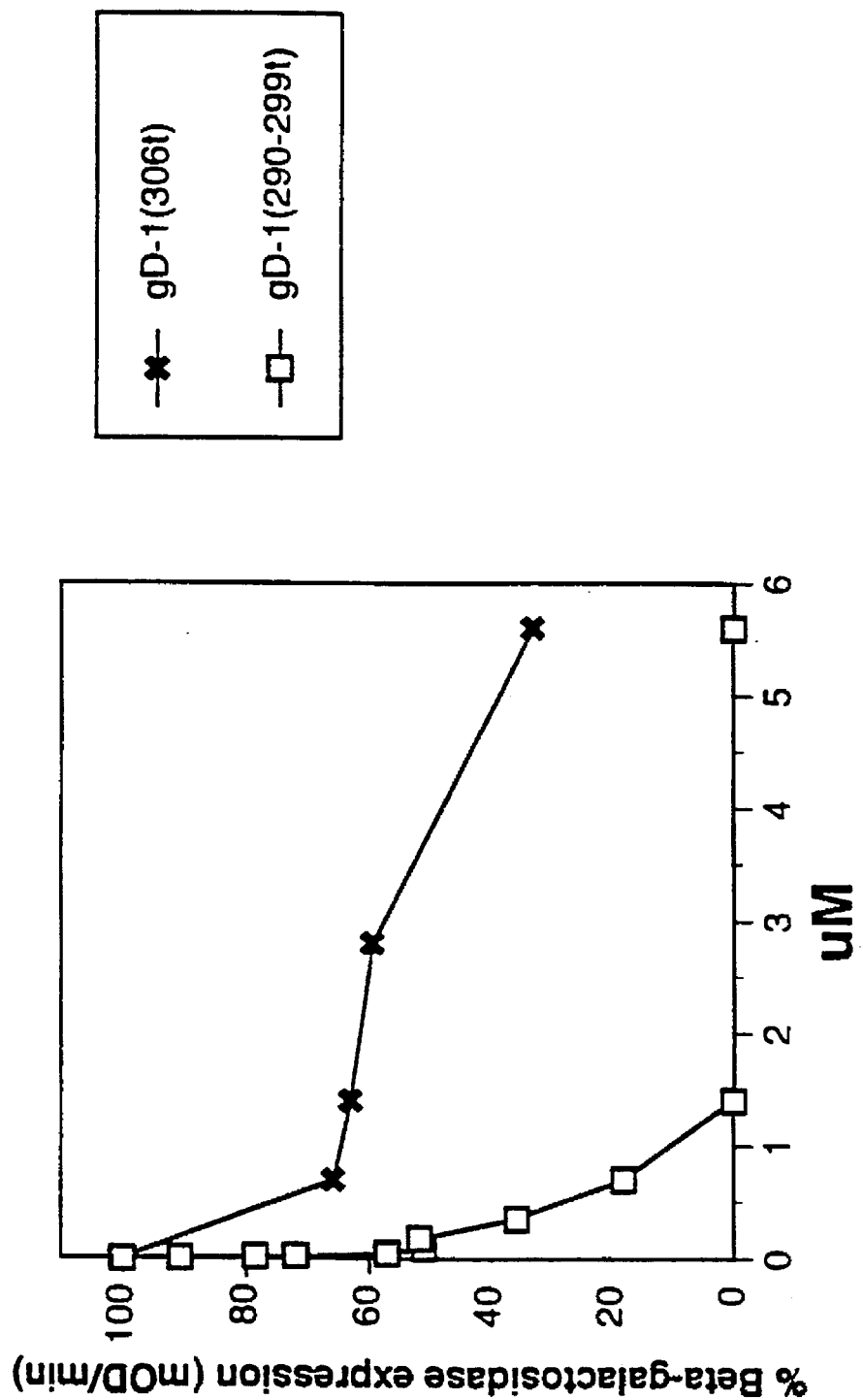
FIG. 7 is a graph depicting the inhibitory effect of gD-1(Δ290–299t) on entry of HSV into Vero cells.

In HSV/lacZ+ assays, confluent Veto cell monolayers in 96 well culture plates were preincubated with variant diluted in DMEM (BioWhittaker, Walkersville, Md.)+5% fetal bovine serum for 90 minutes at 4° C. To each well, $1.5 \times 10^4$ PFU/well of 7134 virus, an HSV-1 KOS strain with both copies of ICP0 gene replaced by $E.\ coli$ lacZ gene [Cal et al., $J.\ Virol.$, 63:4579–4589 (1989)], corresponding to an MOI of about 0.4, was added for 90 minutes at 4° C. After 4 hours incubation at 37° C. the medium was removed and the cells were lysed with 0.5% NP40. The NP40 lysates were transferred to a new 96 well plate. β-galactosidase activity was detected by adding CPRG (Boehringer Mannheim, Indianapolis, Ind.) substrate solution. Absorbance was measured at 570 nm using a Microplate Biokinetics Reader (Bio-Tek Instruments, Winooski, Vt.). Results of the assay are presented in FIG. 7.

Results of the three types of assays are summarized in FIG. 8. It is clear that while the gD-1 variants exhibit similar conformations and cell binding properties that the region IV variant is a significantly more potent HSV inhibitory compound.

While the present invention has been described in terms of specific embodiments, it is understood that variations and modifications will occur to those skilled in the art. For example, corresponding region IV variant gD-2 molecules and other region IV variant gD-1 molecules will be constructed and tested in the same assays for the ability to block HSV-1 and/or HSV-2 infection. Other variants specifically contemplated include, but are not limited to, variants comprising insertions at gD-1 residue 290, variants comprising insertions at gD-1 residue 300, variants comprising deletions of amino acids 277 through 290 and variants comprising deletions of residues 277 through 300. These variants may be made as either full-length or carboxy terminal truncated gD molecules. Accordingly only such limitations as appear in the claims should be placed on the invention.

We claim:

1. A variant herpes simplex virus glycoprotein D molecule comprising amino acids 1 to 300 of SEQ ID NO: 2.

2. The variant molecule of claim 1 further comprising amino acids −2 and −1 of SEQ ID NO: 2.

3. The variant molecule of claim 1 further comprising amino acids 301 to 306 of SEQ ID NO: 2.

4. The gD-1(Δ290–299t) molecule comprising amino acids −2 to 306 of SEQ ID NO: 2.

5. A polynucleotide encoding the protein of claim 1, 2, 3 or 4.

6. The polynucleotide of claim 5 which is a DNA molecule.

7. A DNA vector comprising the polynucleotide of claim 6.

8. The DNA vector of claim 7 wherein said polynucleotide is operatively linked to an expression control DNA sequence.

9. A host cell stably transformed or transfected with a polynucleotide according to claim 6.

10. A method for producing a variant herpes simplex virus glycoprotein D molecule comprising growing a host cell according to claim 9 in a suitable nutrient medium and isolating said protein from the cell or the medium of its growth.

11. A composition comprising a variant molecule according to claims 1, 2, 3, or 4 and an acceptable carrier.

* * * * *

UNITED STATES PATENT AND TRADEMARK OFFICE
CERTIFICATE OF CORRECTION

PATENT NO. : 5,654,174

DATED : August 5, 1997

INVENTOR(S) : COHEN, et al.

It is certified that error appears in the above-identified patent and that said Letters Patent is hereby corrected as shown below:

Col. 1, lines 20-21, replace "alphahexpesvirinae" with --alphaherpesvirinae--.

Col. 1, line 21, replace "simplex virus" with --*simplex virus*--.

Col. 1, line 28, replace "vital" with --viral--.

Col. 1, line 41, replace "Tat-Singer" with --Tal-Singer--.

Col. 1, line 54, replace "anti-vital" with --anti-viral--.

Col. 1, line 58, replace "vital" with --viral--.

Col. 1, line 66, replace "silos" with --sites--.

Col. 3, line 5, replace "vital" with --viral--.

Col. 3, lines 22-23, replace "pelypeptide" with --polypeptide--.

Col. 3, lines 30-31, replace "pest translational" with --post-translational--.

Col. 3, line 38, replace "chime fie" with --chimeric--.

Col. 3, line 48, replace "1HSV" with --HSV--.

Col. 3, line 61, replace "vital" with --viral--.

Col. 4, line 39, replace "(3061)" with --(306t)--.

Col. 4, line 48, replace "Veto" with --Vero--.

UNITED STATES PATENT AND TRADEMARK OFFICE
CERTIFICATE OF CORRECTION

PATENT NO. : 5,654,174

DATED : August 5, 1997

INVENTOR(S) : COHEN, et al.

It is certified that error appears in the above-identified patent and that said Letters Patent is hereby corrected as shown below:

Col. 5, line 33, replace "BglII" with --*Bgl*II--.

Col. 5, line 36, replace "HindIII" with --*Hind*III--.

Col. 5, line 39, replace "HindIII" with --*Hind*III--.

Col. 5, line 41, replace "HindIII" with --*Hind*III--.

Col. 5, line 43, replace "AGTTTGGTGGGAGGAAGATCTTCCTTTGCGGCGCCAC 3'" with -- AGTTTGGTGGGA<u>GGAAGATCTTCC</u>TTTGCGGCGCCAC3'--.

Col. 5, line 45, replace "BglII" with --*Bgl*II--.

Col. 5, line 52, replace "pi-1236" with --pH236--.

Col. 5, line 56, replace "BglII" with --BglII--.

Col. 5, line 60, replace "5'CCCAAGCTTATCCTTAAGGTCTCTTT3'" with -- 5'CCC<u>AAGCTT</u>ATCCTTAAGGTCTCTTT3'--.

Col. 5, line 63, replace "HindIII" with --*Hind*III--.

Col. 5, lines 65-66, replace "5'TCGCGGCGTCCTGGAAGATCTTCCGGATCGACGGGAT" with -- 5'TCGCGGCGTCCT<u>GGAAGATCTTCC</u>GGATCGACGGGAT--.

Col. 6, line 1, replace "BglIII" with --*Bgl*III--.

Col. 6, line 8, replace "5'CCCAAGCTTCCCGCAGACCTGACCCCC3'" with --5'CCC<u>AAGCTT</u>CCCGCAGACCTGACCCCC3'--.

Col. 6, line 11, replace "HindIII" with --*Hind*III--.

UNITED STATES PATENT AND TRADEMARK OFFICE
CERTIFICATE OF CORRECTION

PATENT NO. : 5,654,174

DATED : August 5, 1997

INVENTOR(S) : COHEN, et al.

It is certified that error appears in the above-identified patent and that said Letters Patent is hereby corrected as shown below:

Col. 6, line 21, replace "HindIII" with --*Hind*III--.

Col. 6, line 27, replace "BamHI-BglII" with --*Bam*HI-*Bgl*II--.

Col. 6, line 28, replace "BglII-BamHI" with --*Bgl*II-*Bam*HI--.

Col. 6, line 43, replace "5'TTTTGGATCCCAAATATGCCTTGGCGGATG" with --5'TTTT<u>GGATCCC</u>AAATATGCCTTGGCGGATG--;

Col. 6, line 44, replace "(SEQ 112)NO:12)" with --(SEQ ID NO:12)--;

Col. 6, line 45, replace "BamHI" with --*Bam*HI--;

Col. 6, lines 46-47, replace " GTAGTAGTAGTAATTGACGTCTTTT" with --<u>GTAGTAGTAGTAGTA</u>ATT<u>GACGTC</u>TTTT--;

Col. 6, line 50, replace "PstI" with --*Pst*I--;

Col. 6, line 57, replace "BamHI and PstI" with --*Bam*HI and *Pst*I--;

Col. 8, line 8, replace "1lI" with --III--;

Col. 8, line 20, replace "(SEQ D NO:4)" with --(SEQ ID NO:4)--;

Col. 8, line 25, replace "1/I" with --III--;

Col. 8, line 37, replace "litered" with --titered--;

UNITED STATES PATENT AND TRADEMARK OFFICE
CERTIFICATE OF CORRECTION

PATENT NO. : 5,654,174
DATED : August 5, 1997
INVENTOR(S) : COHEN, et al.

It is certified that error appears in the above-identified patent and that said Letters Patent is hereby corrected as shown below:

Col. 9, line 6, replace "liters" with --titers--;

Col. 9, line 7, replace "mount" with --amount--;

Col. 9, line 13, replace "I11" with --III--;

Col. 9, line 34, replace "Veto" with --Vero--;

Col. 10, line 4 replace "[Cal" with --[Cai--;

Claim 11, replace "an acceptable carrier" with --a carrier--.

Signed and Sealed this

Twenty-third Day of May, 2000

Attest:

Q. TODD DICKINSON

*Attesting Officer*        *Director of Patents and Trademarks*